United States Patent [19]
Tsukamoto et al.

[11] Patent Number: 5,892,065
[45] Date of Patent: Apr. 6, 1999

[54] METHOD FOR PRODUCING PURIFIED EPOXY COMPOUND

[75] Inventors: Suketoshi Tsukamoto; Takami Ono, both of Onoda; Hisao Ikeda; Motohiko Hidaka, both of Funabashi, all of Japan

[73] Assignee: Nissan Chemical Industries, Ltd., Tokyo, Japan

[21] Appl. No.: 892,198

[22] Filed: Jul. 14, 1997

[30] Foreign Application Priority Data

| Jul. 19, 1996 | [JP] | Japan | 8-190574 |
| Oct. 3, 1996 | [JP] | Japan | 8-263320 |
| Oct. 3, 1996 | [JP] | Japan | 8-263321 |
| Nov. 6, 1996 | [JP] | Japan | 8-293769 |
| Nov. 6, 1996 | [JP] | Japan | 8-293770 |
| Nov. 26, 1996 | [JP] | Japan | 8-314682 |
| Nov. 26, 1996 | [JP] | Japan | 8-314683 |

[51] Int. Cl.$^6$ .................... C07D 301/02; C07D 405/12
[52] U.S. Cl. ........................... 549/515; 544/219
[58] Field of Search ............................. 549/515

[56] References Cited

U.S. PATENT DOCUMENTS

| 3,198,241 | 8/1965 | Baird | 159/13.2 |
| 3,859,314 | 1/1975 | Dukes et al. | 549/521 |
| 4,395,542 | 7/1983 | Sury | 528/481 |

FOREIGN PATENT DOCUMENTS 0 028 024  5/1981  European Pat. Off. .

*Primary Examiner*—Bernard Dentz
*Attorney, Agent, or Firm*—Oblon, Spivak, McClelland, Maier & Neustadt, P.C.

[57] ABSTRACT

A 2,3-epoxypropyl derivative or a 2-methyl-2,3-epoxypropyl derivative of a compound having carboxyl groups or amido groups is produced as a purified product having an epoxide equivalent of 1.0 to 1.1 times the theoretical epoxide equivalent of the derivative, an ionic halogen content of 10 ppm or less, transparency when molten and a stability against increase in the epoxide equivalent when stored at 150° C. for 24 hours, by a process comprising steps (A) reacting 1.2 to 60 mol of an epihalohydrin or a 2-methyl-epihalohydrin with 1 mol of active hydrogen atoms of the carboxyl or amido group of the compound in the presence of a particular catalyst, thereby forming a reaction product containing a 2-hydroxy-3-halopropyl derivative or a 2-hydroxy-2-methyl-3-halopropyl derivative, (B) dehydrohalogenating the derivative by adding to the reaction product a sufficient amount of an alkali metal hydroxide thereby forming a final slurry containing the 2,3-epoxypropyl derivative of the 2-methyl-2,3-epoxypropyl derivative and the alkali metal halide, (C) washing the final slurry or a liquid product formed by removing the alkali metal halide from the final slurry thereby forming a refined liquid containing the derivative, and (D) removing by evaporation the epihalohydrin or the 2-methyl-epihalohidrin from the refined liquid, thereby forming the 2,3-epoxypropyl derivative or the 2-methyl-2,3-epoxypropyl derivative as the purified product.

26 Claims, No Drawings

METHOD FOR PRODUCING PURIFIED EPOXY COMPOUND

The present invention relates to an improvement in a method for producing an epoxy compound having 2,3-epoxypropyl groups or 2-methyl-2,3-epoxypropyl groups as a purified product, and in particular to a method for efficiently producing from a compound having in its molecule 2 to 4 carboxyl groups or 1 to 3 amido groups the 2,3-epoxypropyl derivative or the 2-methyl-2,3-epoxypropyl derivative in which all of the hydrogen atoms in the carboxyl groups or the amido groups are replaced by 2,3-epoxypropyl groups or 2-methyl-2,3-epoxypropyl groups as a purified product which forms a transparent and stable liquid when molten.

U.S. Pat. No. 3,859,314 discloses a method for producing a glycidyl ester of a polycarboxylic acid which comprises reacting a polycarboxylic acid with at least 2 mol of epichlorohydrin, per mol of the carboxyl group of the polycarboxylic acid, by using a tertiary amine, a tertiary amine salt or a quaternary ammonium compound as a catalyst at a temperature of from 150° to 200° F. until the acid value becomes 0, and then hydrohalogenating the resulting chlorohydrin ester by gradually adding to the ester an alkali metal hydroxide at a temperature of from 90° to 130° F. under a reduced pressure enough to remove the water generated upon the dehydrohalogenation by evaporation.

The specification of the patent discloses an example in which diglycidyl isophthalate having an epoxide equivalent of 152 and a total chlorine content of 0.8% is produced by a process comprising washing the product resulting from dehydrohalogenation of the chlorohydrin ester of isophthalic acid with water and then removing epichlorohydrin from the product by distillation under reduced pressure. The epoxide equivalent is 1.09 times greater than the theoretical value 139.

Japanese Examined Patent Publication JP-B-44-20323 discloses a method for producing a N-glycidyl derivative of a compound having an amido group, which comprises reacting the compound having an amido group in the presence of a phosphonium halide and then treating the resulting reaction product with an alkaline compound. This publication discloses in examples that a product of triglycidyl isocyanurate was obtained in a 89% yield by washing the product obtained by the method with water, sodium dihydrogenphosphate aqueous solution and then distilled water, and next removing volatile components from the washed product at 110° C. under reduced pressure, that the final product obtained by crystallization from a 50 wt % methanol solution of the product had an epoxide equivalent of 0.92 per 100 g of the product and a chlorine content of 1.0 wt %, and that when the final product was heated at 100° C. for 115 hours, the epoxide equivalent of the final product decreased by 10%.

Japanese Examined Patent Publication JP-B-45-22751 discloses a method for producing a product of triglycidyl isocyanurate, which comprises reacting cyanuric acid with 6 to 30 times the molar quantity of epichlorohydrin in the presence of a catalyst such as a tertiary amine, a quaternary ammonium base or a quaternary ammonium salt at from 60° to 165° C., adding a stoichiometrically 5 to 40% excess of thick alkali hydroxide aqueous solution, washing the resulting reaction product with water, a sodium dihydrogenphosphate aqueous solution or a dilute sodium hydroxide aqueous solution and finally water under stirring, and then removing epichlorohydrin by using a rotary evaporator. In examples in the publication, it is disclosed that the product contains from 9.49 to 9.8 mol of oxirane oxygen per 1 kg and from 0.5 to 1.1% of chlorine.

U.S. Pat. No. 3,198,241 discloses a method for separating and recovering a non-volatile substance from a mixture of the substance and a volatile substance in a fluid, which comprises repeatedly forming a thin film of the fluid on a vertical heat transfer surface by letting the fluid fall down by gravity and evaporating the volatile substance from the falling fluid film by heat transfer from a heat exchange medium.

U.S. Pat. No. 4,395,542 discloses a method wherein triglycidyl isocyanurate containing at least 2,000 ppm of epichlorohydrin and associated volatile substances is heated to a temperature which is high enough to fluidize the triglycidyl isocyanurate but not enough for causing pyrolysis, such as from 143° to 159° C., and then gravitationally passed through a column packed with a fine wire mesh or a multi-stage stripper at a pressure of from 1 to 500 mmHg at least once for multi-stage stripping, to obtain a triglycidyl isocyanurate product containing at most 10 ppm of epichlorohydrin and related volatile substances.

The epoxy compound products obtained by these conventional methods are available for ordinary use, for example, as a starting material of a polyester paint. However, there is a growing demand for these epoxy compounds in the form of high purity industrial products for some purposes. In particular, since these epoxy compounds came into use for semiconductor sealers, conductive bonding adhesives and solder resists, it has been demanded to provide 2,3-epoxypropyl derivatives or 2-methyl-2,3-epoxypropyl derivatives of polycarboxylic acids or compounds having in their molecules at least one amido group, which is useful for such use, in the form of high purity industrial products.

Combinations of the above-mentioned conventional production methods with well-known purification method provide products which somewhat meet the demand for high purity. For example, by repeatedly washing with water the epichlorohydrin solution of a 2,3-epoxypropyl derivative or the 2-methyl epichlorohydrin solution of a 2-methyl-2,3-epoxypropyl derivative obtained in the course of the above-mentioned methods, or by repeatedly recrystallizing a 2,3-epoxypropyl derivative or a 2-methyl-2,3-epoxypropyl derivative as the products of these conventional methods from an alcohol such as methanol, the purities of the products can be improved.

However, since these glycidyl esters and N-glycidyl compounds generally dissolve in water in more than a negligible amount when washed with water, the repeated washing of the product with water as described above leads to a low yield of the product. The above-mentioned purification method by recrystallization is not applicable to products of amorphous epoxy compounds. When the method is applied to a product of a crystalline epoxy compound, because the method can hardly remove fine insoluble impurities in the product, the method can not achieve such radical purification that the product forms a transparent melt when molten.

In the production method disclosed in Japanese Examined Patent Publication JP-B-45-22751, the removal of epichlorohydrin at the end of the method is not efficient because of the use of a rotary evaporator, and the yield of the product is rather low. Thus, this method is disadvantageous for large-scale industrial production. In the method disclosed in Japanese Examined Patent Publication JP-B-44-20323, the removal of epichlorohydrin at the end of the method is carried out by vaporization under reduced pressure, but this publication does not disclose an evaporation method which improves the purity of the product.

In the method disclosed in U.S. Pat. No. 3,198,241, because the falling fluid film is formed by letting the fluid fall down by gravity, a highly viscous fluid such as triglycidyl isocyanurate containing a low concentration of epichlorohydrin can hardly form a thin film in a short time. In the method disclosed in the U.S. Patent, it is necessary to repeat the formation of a fluid film at a high temperature many times. Therefore, not only it takes a long time to remove epichlorohydrin, but also the purity of the product is likely to decrease while the product is maintained at such a high temperature for a long time.

In the method disclosed in U.S. Pat. No. 4,395,542, because the fluid falls down by gravity, a highly viscous fluid such as triglycidyl isocyanurate containing a low concentration of epichlorohydrin does not form a thin film by falling down. The evaporation method by multi-stage stripping can accomplish removal of epichlorohydrin in a short time as compared with the evaporation method by formation of a falling fluid film disclosed in U.S. Pat. No. 3,198,241. However, high-molecular weight compounds adhere to the inner wall of the stripper and thereby prevent smooth heat transfer or contaminate the product after stripping with insoluble matters, especially when the method is conducted in a large-scale apparatus. In particular, a product containing such insoluble matters causes problems of giving a molded article with a low transparency when used for a transparent resin molded article, or giving a coating film with a poor surface smoothness when used as a paint.

The object of the present invention is to provide a method for efficiently producing from a compound having in its molecule 2 to 4 carboxyl groups or 1 to 3 amido groups the 2,3-epoxypropyl derivative or the 2-methyl-2,3-epoxypropyl derivative in which all of the hydrogen atoms in the carboxyl groups or the amido groups are replaced by 2,3-epoxypropyl groups or 2-methyl-2,3-epoxypropyl groups as an industrial product which has a high oxirane oxygen content, a high heat stability and a low ionic halogen content and forms a transparent liquid when molten.

The present invention provides a method for producing the 2,3-epoxypropyl derivative or the 2-methyl-2,3-epoxypropyl derivative of a compound having 2 to 4 carboxyl groups or 1 to 3 amido groups as a purified product which has an epoxide equivalent of 1.0 to 1.1 times the theoretical epoxide equivalent of the derivative and an ionic halogen content of 10 ppm or less, forms a transparent liquid when molten, and shows increasing in epoxide equivalent by at most 3% when stored at 150° C. for 24 hours, comprising steps (A) to (D):

(A) reacting an epihalohydrin or a 2-methyl-epihalohydrin with a compound having in its molecule 2 to 4 carboxyl groups or 1 to 3 amido groups in a reaction mixture containing the compound and the epihalohydrin or the 2-methyl-epihalohydrin in a ratio of 1 mol of active hydrogen atoms of the carboxyl groups or the amido groups of the compound to 1.2 to 60 mol of the epihalohydrin or the 2-methyl-epihalohydrin, and a catalytic amount of a tertiary amine, a quaternary ammonium base or salt, a tri-substituted phosphine or a quaternary phosphonium salt, thereby forming a reaction product containing a 2-hydroxy-3-halopropyl derivative or a 2-hydroxy-2-methyl-3-halopropyl derivative of the compound, (B) adding gradually to the reaction product an alkali metal hydroxide in a ratio of 1 to 2 mol of the hydroxide to 1 mol of active hydrogen atoms of the carboxyl groups or the amido groups of the compound in the reaction product before the reaction in step (A) to cause and complete dehydrohalogenation to the derivative while agitating the resulting slurry containing a precipitated alkali metal halide, thereby forming a final slurry containing the 2,3-epoxypropyl derivative or the 2-methyl-2,3-epoxypropyl derivative of the compound and an alkali metal halide produced by the dehydrohalogenation, (C) washing the final slurry obtained in step (B) or a liquid product obtained by removing the alkali metal halide from the final slurry in step (B) with an aqueous solution of, as refining agent, a sulfonic acid, a salt of a sulfonic acid, a salt of a carboxylic acid having at least 7 carbon atoms in the molecule, a salt of a sulfate of an alcohol having at least 4 carbon atoms in the molecule or a mixture thereof respectively having a solubility of at least 1 wt % in water at 30° C., said solution containing the refining agent in an amount effective for refining the slurry or the liquid product, thereby forming a refined liquid containing the derivative formed in step (B), and (D) removing by evaporation the epihalohydrin or the 2-methyl-epihalohidrin in the refined liquid obtained in step (C), thereby forming the 2,3-epoxypropyl derivative or the 2-methyl-2,3-epoxypropyl derivative of the compound as the purified product.

In the present invention, the epoxide equivalent of a product of an epoxy compound is defined as the weight of the product in grams which contains 1 mol of oxirane oxygen atoms.

The ionic halogen content of a product is determined by ion chromatography analysis of a sample solution of the product obtained by dissolving the product in a liquid mixture of 100 parts by weight of acetonitrile and 25 parts by weight of pure water or extracting the product with the liquid mixture, and represents the content of ionic halogens present in the product in the form of salts.

The heat stability of a product which is represented by the percentage of the difference in epoxide equivalent between the product before and after heating at 150° C. for 24 hours in a sealed vessel, to the epoxide equivalent of the product before the heating. The smaller the percentage of the increase in epoxy equivalent is, the higher the heat stability of the product is evaluated.

The turbidity of the melt of a product is represented by the kaolin turbidity of the melt after deaeration. The kaolin turbidity is defined so that when a mixture of 1 g of kaolin of the guaranteed grade and 10 ml of 37 wt % formalin is diluted with pure water, a 10 ppm kaolin solution is graded 1, a 20 ppm kaolin solution is graded 2, a 30 ppm kaolin solution is graded 3 and a 50 ppm kaolin solution is graded 4. The kaolin turbidity of the melt of a product is represented as the kaolin turbidity rating of a kaolin solution of the same turbidity. The smaller the kaolin turbidity of the melt of a product is, the higher the purity of the product is. A product having a kaolin turbidity of 1 or less is substantially transparent.

The product obtained in the above-mentioned step (D) of the present invention is such a highly purified product that it has an epoxide equivalent of 1.0 to 1.1 times as large as the theoretical epoxide equivalent of the derivative, a heat stability corresponding to an increase of at most 3% in epoxide equivalent, an ionic halogen content of 10 ppm or less and a kaolin turbidity of at most 1 when molten.

The starting compound having in its molecule 2 to 4 carboxyl groups supplied in step (A) may be any compound which is conventionally used as a starting material of an epoxy compound. For example, aliphatic dicarboxylic acids such as maleic acid, succinic acid, itaconic acid, God fumaric acid, adipic acid, pimelic acid, suberic acid, sebacic acid or dimer acids or trimer acids derived from unsaturated fatty acids; aromatic dicarboxylic acids such as phthalic acid, isophthalic acid, terephthalic acid, tetrahydrophthalic acid, hymic acid, tetrachlorophthalic acid, hexahydrophthalic acid, phenylenediacetic acid or naphthalic acid; aromatic tricarboxylic acids such as trimellitic acid or trimesic acid; and aromatic tetracarboxylic acids such as pyromellitic acid may be mentioned. As one carboxyl group has one active hydrogen atom, a dicarboxylic acid, a tricarboxylic acid and a tetracarboxylic acid have 2, 3 and 4 active hydrogen atoms per molecule, respectively. Acid anhydrides derived from these compounds having carboxylic groups may be used as long as they react as the compound having carboxyl groups used in step (A). The number of active hydrogen atoms in one molecule of such an acid anhydride is represented by the number of all carboxyl groups in one molecule of the hydrolyzate of the acid anhydride. Preferred examples of the compound having 2 to 4 carboxyl groups are phthalic acid, isophthalic acid, terephthalic acid, trimellitic acid, trimesic acid and pyromellitic acid.

As the compound having in its molecule 1 to 3 amido groups, those which are conventionally used as a starting material of an epoxy compound may be used. For example, N,N'-dimethylurea, N,N'-diphenylurea, ethylene urea, hydantoin and isocyanuric acid may be mentioned. Among them, hydantoin and isocyanuric acid are preferred. Ethylene urea, N,N'-dimethylurea and N,N'-diphenylurea have one amide group and two active hydrogen atoms each. Hydantoin has two amido groups and two active hydrogen atoms. Isocyanuric acid has three amido groups and three active hydrogen atoms.

As the epihalohydrin, epichlorohydrin, epibromohydrin and epiiodohydrin may be mentioned. Among them, epichlorohydrin readily is preferred due to its easy availability. As the 2-methylepihalohydrin, 2-methylepichlorohydrin, 2-methylepibromohydrin and 2-methylepiiodohydrin may be mentioned. 2-Methylepichlorohydrin is preferred in view of its easy availability.

As the catalyst, an amine, a quaternary ammonium compound, a substituted phosphine, a quaternary ammonium compound and the like may be used. Although a primary amine such as butylamine and a secondary amine such as dibutylamine may be used, preferred catalysts are tertiary amines, quaternary ammonium bases, quaternary ammonium salts, tri-substituted phosphines and quaternary phosphonium salts.

Preferred catalysts are, for example, tertiary amines such as triethylamine, tri-n-propylamine, tributylamine, benzyldimethylamine or triethanolamine; quaternary ammonium hydroxides such as tetramethylammonium hydroxide or benzyltrimethylammonium hydroxide; quaternary ammonium salts such as benzyltrimethylammonium chloride, benzyltrimethylammonium acetate, methyltriethylammonium chloride, tetramethylammonium chloride or tetraethylammonium chloride; tri-substituted phosphines such as triphenylphosphine, tritolylphosphine or tributylphosphine; and quaternary phosphonium salts such as methyltriphenylphosphonium bromide, methyltriphenylphosphonium chloride, ethyltriphenyl chloride, methyltriphenylphosphonium iodide, benzyltriphenylphosphonium bromide or ethyltriphenylphosphonium bromide. Above all, tetramethylammonium chloride, tetraethylammonium bromide and ethyltriphenylphosphonium bromide are preferred. When terephthalic acid is used as the starting material, an alkali metal halide such as sodium bromide may be used as a catalyst.

As examples of an alkali metal hydroxide, sodium, potassium and lithium hydroxides may be mentioned. Among them, sodium hydroxide and potassium hydroxide are preferred. Such an alkali metal hydroxide is preferably used in the form of a thick aqueous solution, for example, of a concentration of 20 to 70 wt %, preferably from 40 to 60 wt %.

In step (A), four types of starting material may be used. The first type consists of the above-mentioned compound having carboxyl groups and an epihalohydrin, the second one consists of the above-mentioned compound having carboxyl groups and a 2-methylepihalohydrin, the third one consists of the the above-mentioned compound having amido groups and an epihalohydrin, and the fourth one consists of the above-mentioned compound having amido groups and a 2-methyleipihalohydrin. Whichever type of starting material may be used, the epihalohydrin or the 2-methylepihalohydrin is used in a ratio of 1.2 to 60 mol, preferably from 2 to 20 mol, and most preferably from 5 to 10 mol, to 1 mol of active hydrogen atoms in the compound having carboxyl groups or the compound having amido groups.

In step (A), the compound having carboxyl groups or amido groups undergoes addition reaction with the epihalohydrin or the 2-methylepihalohydrin, to form the 2-hydroxy-3-halopropyl derivative or the 2-hydroxy-2-methyl-3-halopropyl derivative of the compound having carboxyl groups or amido groups. Therefore, a dicarboxylic acid like those described above forms its bis(2-hydroxy-3-halopropyl)ester or its bis(2-hydroxy-2-methyl-3-halopropyl)ester, a tricarboxylic acid like those described above forms its tris(2-hydroxy-3-halopropyl)ester or its tris(2-hydroxy-2-methyl-3-halopropyl)ester, and a tetracarboxylic acid like those described above forms its tetrakis(2-hydroxy-3-halopropyl)ester or its tetrakis(2-hydroxy-2-methyl-3-halopropyl)ester, respectively. On the other hand, a urea derivative like those described above forms its N,N'-bis(2-hydroxy-3-halopropyl)derivative or its bis(2-hydroxy-2-methyl-3-halopropyl)derivative, hydantoin forms its N,N'-bis(2-hydroxy-3-halopropyl)derivative or its bis(2-hydroxy-2-methyl-3-halopropyl)derivative, and isocyanuric acid forms its tris(2-hydroxy-3-halopropyl)ester or its tris(2-hydroxy-2-methyl-3-halopropyl)ester, respectively.

Although the addition reaction in step (A) may be conducted in the absence of a catalyst, a substance which accelerate the reaction is preferably used to accelerate the reaction. A wide variety of substances ranging from those having a relatively weak action like alkali metal hydroxides such as sodium hydroxide, to the above-mentioned catalysts which have a relatively strong action may be used. However, it is preferred to use the above-mentioned preferred catalysts to accelerate the reaction. Therefore, the addition reaction is conducted in a reaction mixture consisting of the above-mentioned starting material and a tertiary amine, a quaternary ammonium base, a quaternary ammonium salt, a tri-substituted phosphine or a quaternary phosphonium salt as a catalyst, under heating, preferably at a temperature of from 60° to 130° C. The amount of the catalyst is in a ratio of 0.001 to 0.1 mol, preferably 0.01 to 0.05 mol of the catalyst to 1 mol of a compound having carboxyl groups or amido groups. The above molar ratio is also preferably applicable to an alkali metal halide catalyst which may be used when terephthalic acid is used as a starting material in the reaction. In the above reaction mixture, 0.1 to 2 wt % of water, based on the epihalohydrin or the 2-methylhalohydrin therein, may be incorporated from the beginning, to accelerate the reaction.

The reaction mixture is heated until at least 90% of, preferably all the active hydrogen atoms of the compound having carboxyl groups or amido groups in the reaction mixture disappears. Active hydrogen atoms in the reaction mixture can be detected, for example, by liquid chromatography analysis. Thus, by heating usually for 2 to 10 hours, a reaction product containing an epihalohydrin and the above-mentioned 2-hydroxy-3-halopropyl derivative, or a reaction product containing a 2-methylepihalohydrin and the above-mentioned 2-hydroxy-2-methyl-3-halopropyl derivative is produced.

In step (B), the 2-hydroxy-3-halopropyl derivative and the by-product 2-hydroxy-1,3-dihalopropane, or the 2-hydroxy-2-methyl-3-halopropyl derivative and the by-product 2-hydroxy-2-methyl-1,3-dihalopropane in the reaction product obtained in step (A) undergo dehydrohydrogenation to epoxy compounds with release of a hydrogen halide.

Accordingly in the reaction, the by-product 2-hydroxy-1, 3-dihalopropane forms an epihalohydrin, and the by-product 2-hydroxy-2-methyl-1,3-dihalopropane forms a 2-methylepihalohydrin, respectively.

On the other hand, the bis(2-hydroxy-3-halopropyl)ester of a dicarboxylic acid produced in step (A) forms the bis(2,3-epoxypropyl)ester of the dicarboxylic acid, and the bis(2-hydroxy-2-methyl-3-halopropyl)ester of a dicarboxylic acid forms the bis(2-methyl-2,3-epoxypropyl)ester of the carboxylic acid.

Similarly, the tris(2-hydroxy-3-halopropyl)ester of a tricarboxylic acid forms the tris(2,3-epoxypropyl)ester of the tricarboxylic acid, and the tris(2-hydroxy- 2-methyl-3-halopropyl)ester of a tricarboxylic acid forms the tris(2-methyl-2,3-epoxypropyl)ester of the tricarboxylic acid.

The tetrakis(2-hydroxy-3-halopropyl)ester of a tetracarboxylic acid forms the tetrakis(2,3-epoxypropyl)ester of the tetracarboxylic acid, and a tetrakis(2-hydroxy-2-methyl-3-halopropyl)ester of a tetracarboxylic acid forms the tetrakis (2-methyl-2,3-epoxypropyl)ester of the tetracarboxylic acid, respectively.

A N,N'-bis(2-hydroxy-3-halopropyl)derivative of a urea derivative forms the N,N'-bis(2,3-epoxypropyl)derivative of the urea derivative, and a N,N'-bis(2-hydroxy-2-methyl-3-halopropyl)derivative of a urea derivative forms the N,N'-bis(2-methyl-2,3-epoxypropyl)derivative of the urea derivative.

A N,N'-bis(2-hydroxy-3-halopropyl) derivative of hydantoin forms the N,N'-bis(2,3-epoxypropyl)derivative of hydantoin, and a N,N'-bis(2-hydroxy-2-methyl-3-halopropyl)derivative of hydantoin forms the N,N'-bis(2-methyl-2,3-epoxypropyl)derivative of hydantoin, respectively.

A tris(2-hydroxy-3-halopropyl)ester of isocyanuric acid forms the tris(2,3-epoxypropyl)ester of isocyanuric acid, and a tris(2-hydroxy-2-methyl-3-halopropyl)ester of isocyanuric acid forms the tris(2-methyl-2,3-epoxypropyl)ester of isocyanuric acid, respectively.

In Step (B), an alkali metal hydroxide, preferably in 20–70 wt % aqueous solution, more preferably in 40–60 wt % aqueous solution is added gradually, preferably dropwise, to the reaction product obtained in step (A), in a ratio of 1 to 2 mol, preferably 1 to 1.2 mol of the hydroxide to 1 mol of the active hydrogen atoms of the carboxyl groups or the amido groups of the compound in the reaction product before the preceding addition reaction, while the epihalohydrin or the 2-methylepihalohydrin in the reaction product is refluxed. Upon the addition of an alkali metal hydroxide, the above-mentioned dehydrohalogenation reaction takes place to generate an alkali metal halide and water in the reaction mixture. The alkali metal halide crystallizes out to give a slurry containing the precipitated alkali metal halide. The dehydrohalogenation reaction is accelerated when conducted in the presence of from 5 to 30 wt %, based on the epihalohydrin in the slurry, of an aprotic polar solvent such as dimethylformamide or methyl isobutyl ketone, and thereby it is possible to reduce the content of hydrolytic halogen in the product obtained later in step (D). When the reaction is conducted in the presence of the above-mentioned amount of an aprotic polar solvent, though the solvent may be previously added to a reaction mixture in step (A), the solvent is preferably added to the slurry in step (B), which is conducted at a relatively lower temperature, to accelerate the reaction.

While the slurry is thus formed, the slurry is maintained under reduced pressure at as low a temperature as possible, for example, at from 10° to 80° C., preferably at from 20° to 70° C., to continuously evaporate the added water and the generated water along with the epihalohydrin or the 2-methylepihalohydrin in the slurry, and the vapor is condensed by a condenser so that the condensed water drains away off the reaction mixture and the condensed epihalohydrin or 2-ethylepihalohydrin returns to the slurry. Further, during the addition, it is preferred to maintain the degree of vacuum around 100 mmHg at the beginning and then gradually increase the degree of vacuum as the addition progresses, to about 60 mmHg finally. The reaction in step (B) completes usually in 1 to 10 hours.

The reaction in step (B) is preferably carried out under agitation of the slurry. When the reaction is carried out on a small scale, ordinary agitation, for example, by means of paddle blades or turbine blades, is satisfactory. However, when the reaction in step (B) is conducted on a large scale, for example, in a slurry of a volume of at least 20 l, ordinary agitation is inadequate. If agitation is inadequate, the above-mentioned precipitated alkali metal halide, water and an alkali metal hydroxide accumulate or adhere in bulk on the bottom and the wall of the vessel where a fluid is unlikely to flow smoothly, and thereby prevent water from smooth evaporation. Such inadequate dispersion of a precipitated alkali metal halide, water and an alkali metal hydroxide tends to cause a side reaction where they accumulate, and thereby leads to low yields and low purities of the products obtained subsequent steps (C) and (D). However, it has been found that when the slurry is maintained under agitation enough to prevent accumulation of a precipitated alkali metal halide, water and an alkali metal hydroxide, the yield and the purity of the product can be maintained at high levels.

Merely high speed rotation of an agitator equipped with puddle or turbine blades is not effective to keep the slurry, especially of a large volume of at least 100 l, free from accumulation of a precipitated alkali metal halide, water and an alkali metal hydroxide. As the reaction proceeds, an alkali metal halide would increasingly precipitate in the slurry to a high concentration enough to produce a large resistance to the agitator rotating at a high speed. Sometimes, such high speed rotation of an agitator ends up merely pressing the precipitated alkali metal halide, water and an alkali metal hydroxide against the wall of the vessel. Further, in the case of a slurry of a large volume, water in the slurry readily evaporates near the slurry surface, but hardly boils at the bottom of the reaction vessel. Therefore, if a precipitated alkali metal halide, water and an alkali metal hydroxide stay still together at the bottom of a reaction vessel, a side reaction tends to occur there in the slurry.

It is not so important to produce a high speed flow of the slurry, and agitation which gives a localized circulating flow in the slurry is not effective, either. Instead, agitation which maintains uniform dispersion throughout the slurry is preferred. Preferred agitation is for example, such that it causes the slurry to produce a stream circulating and ascending from the bottom along the inner side wall of a vessel to the surface of the slurry, turning there the ascending stream to a stream swirling downward and shearing across the swirling stream, thereby maintaining the slurry uniform. Agitators which produce such a circulating stream and a swirling stream and shears the swirling stream into fragments are already known and commercially available. An agitator which performs such preferred agitation can provide more preferred agitation when used in combination with a reaction vessel equipped with baffles.

Accordingly, when a large volume slurry of at least 100 l is dealt with, step (B) is carried out in a vessel by a process (B') comprising gradually adding to the reaction product obtained in step (A), from 1 to 2 mol, preferably from 1 to 1.2 mol of an alkali metal hydroxide, per 1 mol of the active hydrogen atoms in the compound contained in the reaction product before the preceding addition reaction, as an aqueous solution having a concentration of 20 to 70 wt %, preferably 40 to 60 wt % of the hydroxide, to form a slurry containing a precipitated alkali metal halide, and maintaining the slurry under agitation which causes the slurry to produce a stream circulating and ascending from the bottom along the inner side wall of the vessel to the surface of the slurry, turning there the ascending stream to a stream swirling downward and shearing across the swirling stream, thereby maintaining the slurry uniform, while removing by evaporation from the slurry the water added and generated in a vacuum at a temperature of 20° to 60° C. until the dehydrohalogenation reaction is completed, to form a slurry containing a precipitated alkali metal halide and the 2,3-epoxypropyl derivative of the compound having carboxyl groups or amido groups and an epihalohydrin, or the 2-methyl-2,3-epoxypropyl derivative of the compound and a 2-methylepihalohydrin. The process (B') can remarkably reduce the amount of by-product impurities in the reaction product and therefore, is advantageous in production of a crystalline derivative such as the tris(2,3-epoxypropyl)ester or the tris(2-methyl-2,3-epoxypropyl)ester of isocyanuric acid, or the bis(2,3-epoxypropyl)ester or the bis(2-methyl-2,3-epoxypropyl)ester of terephthalic acid, because the purity of the product can be drastically improved later in step (E).

As the refining agent used in step (C), a water-soluble organic group-containing compound which has a solubility of at least 1 wt % in water at 30° C. is used. If an organic group-containing compound having a solubility lower than 1 wt % in water at 30° C. was used as a refining agent, the low solubility compound in aqueous solution would migrate to an adjacent organic layer and remains in the product collected in a subsequent step to lower the quality of the product. Notwithstanding that the solubility of an organic group-containing compound in water tends to decrease with an increase in the number of carbon atoms in the organic group of the compound, compounds which contain an organic group and have a solubility of at least 1 wt % in water at 30° C. are preferred. As a refining agent, although a compound which gives an acidic or alkaline aqueous solution when dissolved in water may be used if the resulting reduction in the yield of the product or the resulting reduction in efficiency due to necessity of an extra washing step is tolerable, a compound which gives a neutral aqueous solution when dissolved in water is preferred because it does not cause such a reduction in efficiency.

As a compound used as a refining agent, a sulfonic acid, a salt of a sulfonic acid, a salt of a carboxylic acid, a salt of a sulfate of an alcohol or a mixture thereof may be mentioned. These compounds may contain a hydrocarbon group, an amido group, an ester group, a hydroxyl group, an ether group, an acetoxy group or a hydrocarbon group substituted with such a group. As the above-mentioned salts, salts of monoacidic bases which impart a high solubility to a salt, for example, salts of alkali metals such as sodium, potassium or lithium, salts of amines such as monoethanolamine, diethanolamine or triethanolamine or ammonium salts are preferred, rather than salts of polyacidic bases such as magnesium, calcium or aluminum.

Preferred examples of a sulfonic acid include benzenesulfonic acid, benzenesulfonic acids substituted with an alkyl having 1 to 3 carbon atoms such as toluenesulfonic acid and xylenesulfonic acid, and naphthalenemonosulfonic acid.

Preferred examples of a salt of a sulfonic acid are alkali metal salts, ammonium salts or amine salts of aromatic sulfonic acids, for example, an alkali metal salt such as the sodium salt, the ammonium salt or an amine salt such as the triethanolamine salt of benzenesulfonic acid, an alkali metal salt such as the sodium salt, the ammonium salt or an amine salt such as the triethanolamine salt of a benzenesulfonic acid substituted with an alkyl group having 1 to 3 carbon atoms such as toluenesulfonic acid, a formaldehyde condensate of such a salt of an alkyl-substituted benzenesulfonic acid, an alkali metal salt such as the sodium salt, the ammonium salt or an amine salt such as the triethanolamine salt of p-hydroxybenzenesulfonic acid, an alkali metal salt such as the sodium salt, the ammonium salt or an amine salt such as the triethanolamine salt of p-nonylbenzenesulfonic acid, an alkali metal salt such as the sodium salt, the ammonium salt or an amine salt such as the triethanolamine salt of naphthalenesulfonic acid or an alkali metal salt of aromatic sulfonic acid such as a formaldehyde condensate of a salt of naphthalenesulfonic acid; alkali metal salts, the ammonium salts or amine salts of alkanesulfonic acids having at most 10 carbon atoms, for example, an alkali metal salt such as the sodium salt, the ammonium salt or an amine salt such as the triethanolamine salt of methanesulfonic acid, an alkali metal salt such as the sodium salt, the ammonium salt or an amine salt such as the triethanolamine salt of ethanesulfonic acid, an alkali metal salts such as the sodium salt, the ammonium salt or an amine salt such as the triethanolamine salt of vinylsulfonic acid, a polymer of such a salt of vinylsulfonic acid, an alkali metal salt such as the sodium salt, the ammonium salt or an amine salt such as the triethanolamine salt of 2-aminoethanesulfonic acid, an alkali metal salt such as the sodium salt, the ammonium salt or an amine salt of the triethanolamine salt of octyl sulfoacetate, an alkali metal salt such as the sodium salt, the ammonium salt or an amine salt such as the triethanolamine salt of butanesulfonic acid, an alkali metal salt such as the sodium salt, the ammonium salt or an amine salt such as the triethanolamine salt of hexanesulfonic acid, an alkali metal salt such as the sodium salt, the ammonium salt or an amine salt such as the triethanolamine salt of octanesulfonic acid, or an alkali metal salt such as the sodium salt, the ammonium salt or an amine salt such as the triethanolamine salt of decanesulfonic acid.

Preferred examples of a salt of a carboxylic acid are alkali metal salts of monobasic alkanoic acids having at most 11 carbon atoms, for example, an alkali metal salt such as the sodium salt of heptanoic acid, an alkali metal salt such as the sodium salt of octanoic acid or an alkali metal salt such as the sodium salt of decanoic acid; alkali metal salts of aromatic monobasic carboxylic acids such as sodium benzoate, sodium salicylate or sodium cinnamate; dialkali metal salts of aromatic dibasic carboxylic acids such as disodium phthalate; di-alkali metal salts of alicyclic hydrocarbon dicarboxylic acids such as disodium hexahydrophthalate; and alkali metal salts of hydroxybenzenecarboxylic acids such as sodium o-hydroxybenzoate or sodium p-hydroxybenzoate.

Preferred examples of a salt of a sulfate of an alcohol are an alkali metal salt such as the sodium salt, the ammonium salt or an amine salt such as the triethanolamine salt of butylsulfate ester, an alkali metal salt such as the sodium salt, the ammonium salt or an amine salt such as the triethanolamine salt of heptylsulfate ester, an alkali metal salt such as the sodium salt, the ammonium salt or an amine salt such as the triethanolamine salt of octylsulfate ester, an alkali metal salt such as the sodium salt, the ammonium salt or an amine salt such as the triethanolamine salt of decylsulfate ester, an alkali metal salt such as the sodium salt, the ammonium salt or an amine salt such as the triethanolamine salt of laurylsulfate ester, an alkali metal salt such as the sodium salt, the ammonium salt or an amine salt such as the triethanolamine salt of myristylsulfate ester, an alkali metal salt such as the sodium salt, the ammonium salt or an amine salt such as the triethanolamine salt of the sulfate of lauryl diethylene glycol ether, and an alkali metal salt such as the sodium salt, the ammonium salt or an amine salt such as the triethanolamine salt of the sulfate of nonyl phenol polyethylene glycol ether. Alkali metal salts of a sulfate of an alcohol having 10 to 28 carbon atoms such as alkali metal salts such as the sodium salt of the sulfate of lauryl polyethylene glycol ether may be used.

Particularly preferred compounds are the sodium salt, the potassium salt, the lithium salt, the ammonium salt or the triethanolamine salt of benzenesulfonic acid, the sodium salt, the potassium salt, the lithium salt, the ammonium salt or the triethanolamine salt of toluenesulfonic acid, the sodium salt, the potassium salt, the lithium salt, the ammonium salt or the triethanolamine salt of vinylsulfonic acid or polymers of these vinylsulfonic acid salts, the sodium salt, the potassium salt, the lithium salt, the ammonium salt or the triethanolamine salt of laurylsulfate, water-soluble formaldehyde condensates of the sodium salt, the potassium salt, the lithium salt, the ammonium salt or the triethanolamine salt of naphthalenesulfonic acid, the sodium salt, the potassium salt or the lithium salt of cinnamic acid, the sodium salt, the potassium salt or the lithium salt of salicylic acid, the disodium salt, dipotassium salt or the dilithium salt of tetrahydrophthalic acid, the disodium salt, the dipotassium salt or the dilithium salt of phthalic acid, toluenesulfonic acid, benzenesulfonic acid and the like. Use of these compounds as a refining agent improves the heat stability of the product collected in a subsequent step and the transparency of its melt. Most preferred are aromatic sulfonic acids and their alkali metal salts, since they do not remain in the product collected in a subsequent step and hardly produce deterioration in the quality of the product attributable to a refining agent.

In step (C), washing the slurry allows the alkali metal halide, the remaining catalyst, the remaining alkali metal hydroxide and other impurities in the slurry to migrate from the slurry to an aqueous layer on contact to give a refined liquid. The aqueous layer contains in addition to these mobile components, small amounts of the epihalohydrin and the 2,3-epoxypropyl derivative, or the 2-methylepihalohydrin and the 2-methyl-2,3-epoxypropyl derivative which was originally contained in the slurry in the dissolved state. Therefore, in the refining, it is advantageous to use a minimum amount of water in view of the yield of the product and to finish washing in an minimum time to improve the production efficiency.

When the slurry is washed with an aqueous solution of an above-mentioned compound as a refining agent, refinement is effected satisfactorily with a relatively small amount of water in a short time to yield a refined liquid without transferring the refining agent from the aqueous layer to the organic layer, and in particular, to such an extent that the product collected in subsequent step (D) has, surprisingly, a kaolin turbidity of at most 1 when molten.

The slurry is washed preferably a few times rather than once. Although the effect of a refining agent increases with its amount, once its amount exceeds 5 wt %, its effect does not increase in proportion to its amount. When the slurry is washed repeatedly as described above, it is preferred that an aqueous solution containing from 0.01 to 5 parts by weight, preferably from 0.05 to 2 parts by weight, most preferably from 0.1 to 1 part by weight, per 100 parts by weight of the derivative in the slurry, of a refining agent is used for the first and the second time, and the amount of the refining agent in an aqueous solution is reduced to 0.001–5 parts by weight, preferably to 0.001–2 parts by weight, most preferably 0.001–1 part by weight, per 100 parts by weight of the derivative in the slurry for the third time to prevent the resulting product from being contaminated with the refining agent. The amount of water used for washing the slurry is preferably 0.5–50 times, in particular 1–5 times the weight of the 2,3-epoxypropyl derivative or the 2-methyl-2,3-epoxypropyl derivative in the slurry each time. When washed with an aqueous solution of a refining agent which has a relatively low solubility in water, the slurry is preferably washed further with a small amount of pure water thereafter. A weakly acidic neutralizer such as sodium dihydrogenphosphate may coexist in the aqueous solutions used for washing. The temperature of the aqueous solutions used for washing is preferably about from 10° to 40° C., more preferably from 20° to 30° C.

The washing is carried out by bringing the slurry layer into contact with the aqueous solution by means of various conventionally known apparatuses either in batches or continuously. For example, the washing can be carried out by introducing the slurry and the above-mentioned amounts of a refining agent and water separately or simultaneously as an aqueous solution into a vessel equipped with an agitator and bringing the slurry layer and the washing aqueous layer into good contact by agitation. The agitation time depends on the intensity of agitation, but agitation is usually continued for a short time such as about 5 to 10 minutes. After the agitation, the liquid in the vessel is allowed to stand. The standing time depends on the intensity of the above agitation, but is 5–60 minutes, preferably 10–30 minutes in the case of usual agitation.

However, the washing of the slurry layer with the aqueous solution in a vessel by agitation can results in a still turbid organic layer, like in case where an insufficiency of a refining agent is used in the aqueous solution. It has been found out that fine droplets of the organic layer produced to secure good contact of the slurry layer with the layer of the washing aqueous solution comparatively readily unify to form an organic layer again, whereas fine droplets of the aqueous solution do not readily unify and therefore remain dispersed in the re-formed organic layer for a long time and make the organic layer turbid. It has been also found out that the re-formed aqueous layer does not contain so large an amount of fine droplets of the organic layer, whereas when an organic layer is collected with fine droplets of the aqueous solution dispersed therein, the organic layer yields a low purity product after evaporation of an epihalohydrin from the organic layer in subsequent step (D). It is believed that certain impurities migrated from the organic layer to around the surfaces of the droplets could serve to maintain the droplets dispersed stably in the organic layer.

It has been found that a high purity product can be produced efficiently by a preferred process for washing the slurry which comprises introducing droplets of the aqueous solution having a mean diameter of 0.1 to 10 mm into a column of the slurry layer, allowing the droplets in contact with the slurry to ascend in the column of the slurry layer and thereafter to unify to form a layer of the aqueous solution or to unify with a previously formed layer of the aqueous solution, and separating the aqueous solution from the slurry layer. The washing process by means of droplets is preferably applied to a liquid product which is obtained by removing of the precipitated alkali metal halide in the slurry obtained in step (B) by stirring the slurry containing the precipitated alkali metal halide obtained in step (B) gently together with a sufficient amount of water or the aqueous solution to dissolve the precipitated alkali metal halide, preferably a few times as much by weight as the slurry or by filtering the slurry containing the precipitated alkali metal halide. The preferable washing process by means of droplets can yield a clear refined liquid, and its efficiency can be still improved by introducing again the layer of the aqueous solution formed previously upon the unification into upper part of the column as droplets having a mean diameter of 0.1 to 10 mm, and allowing the droplets again to ascend and thereafter unify repeatedly. Accordingly, step (C) is preferably carried out for the liquid product obtained by removing the precipitated alkali metal halide, by a process (C') comprising introducing into a column of the layer of the liquid product droplets of the aqueous solution containing a refining agent with a mean diameter of 0.1 to 10 mm, preferably 0.3 to 10 mm, allowing the droplets to ascend and thereafter to unify to form a layer of the aqueous solution in the column, repeating stepwise in the column the cycle consisting of the introducing, the ascending and the unification of the droplets, and continuing supplying to the liquid product the aqueous solution by the introduction thereof until 0.01 to 5 parts by weight of the refining agent relative to 100 parts by weight of the derivative in the liquid product is supplied to the liquid product, thereby forming a refined liquid. The amount of the water supplied with the refining agent in the process (C') is preferably about 50 to 5,000 parts by weight relative to 100 parts by weight of the derivative, and the process (C') can be repeated.

The process (C') has such a high refining effect that it can achieve advantageous refinement even if applied to a liquid product containing a large amount of impurities as obtained without employing the preferred process (B') in step (B). Further, the process (C') can achieve effective refinement without leaving of the aqueous solution in the organic layer even if the amount of a refining agent is reduced. As an extreme example, it is mentioned that the washing process (C') even by using water containing no refining agent can produce an improvement of refining in a short time over the process wherein an organic layer and water are agitated in a vessel and then allowed to stand for a long time followed by collection of the organic layer. In particular, since in the case of production of a crystalline derivative such as the tris(2,3-epoxypropyl)ester or the tris(2-methyl-2,3-epoxypropyl)ester of isocyanuric acid, or the bis(2,3-epoxypropyl)ester or the bis(2-methyl-2,3-epoxypropyl)ester of terephthalic acid, the purity can be increased further in subsequent refining step (E), the washing process (C') by using water containing no refining agent, namely the process (C") which comprises introducing into a column of a layer of the liquid product obtained by removing the precipitated alkali metal halide droplets of water containing no refining agent with a mean diameter of 0.1 to 10 mm, preferably 0.3 to 10 mm, allowing the droplets to ascend in the layer of the liquid product and thereafter to unify to form a water layer in the column, introducing the water layer again as droplets with a mean diameter of 0.1 to 10 mm, preferably 0.3 to 10 mm into the upper part of the column, followed by similarly the ascending and the unification, as repeating of the cycle consisting of the introducing, the ascending and the unification of the droplets in the column, and continuing supplying to the liquid product the water by the introduction thereof until 50 to 5,000 parts by weight of water relative to 100 parts by weight of the derivative in the liquid product, is favorable for production of products of these crystalline derivative. The process (C") can be repeated.

The process which repeats the introduction of droplets of an aqueous solution with a mean diameter of 0.1 to 10 mm, their ascending and their unification into a layer of the aqueous solution can be carried out by using an apparatus designed for such a process. For example, the apparatus comprises a main cylinder, a cylindrical reservoir which is connected above to the upper end of the main cylinder, another cylindrical reservoir which is connected below to the lower end of the main cylinder, a cap which covers the upper reservoir, and a rotating shaft extending to the lower end of the main cylinder through the center of the cap. The upper reservoir has almost the same inner diameter as the main cylinder, is high enough to store a liquid, and has a drain hole in its upper part. Through the cap, there is equipped a liquid supply pipe which extends nearly to the lower end of the upper reservoir. The lower reservoir has almost the same inner diameter as the main cylinder, is deep enough to store a liquid and has a drain hole at the bottom. At the middle of the lower reservoir, there is a liquid supply pipe extending nearly to the lower end of the rotating shaft through its side wall. Around the rotation shaft, a plurality of discs having many holes are provided at a constant interval from the lower end of the shaft about to the upper end of the main cylinder. On the inner side wall of the main cylinder, there are a plurality of doughnut baffles each interposed between the every disc. A hoop ring is fitted underneath the periphery of each disc. Holes are opened in each disc through it from the upper surface to the lower surface so that droplets having a mean diameter of 0.1 to 10 mm are generated through them. The rotating shaft rotates reciprocally by a certain rotation angle, when driven by a driving system connected to its top end.

An organic fluid which is immiscible in water and has a greater specific gravity than water is introduced into the above-mentioned washing apparatus through the supply line connected to the cap until the upper reservoir is filled half. While the rotating shaft is rotated reciprocally, an aqueous solution for washing is supplied to the supply pipe extending from the lower reservoir. The aqueous solution is released in the organic fluid through the outlet of the supply pipe and caught in the ring fitted on the lowermost disc, and passes through its holes, forming droplets in the organic fluid. The droplets are released upward in the column of the organic fluid above the disc and dispersed in the organic fluid while ascending. The baffles fixed to the inner wall of the main cylinder direct the dispersed droplets toward the center of the main cylinder so that the droplets are caught and unify to form the solution layer in the ring fitted on the second lowermost disc. Thereafter, the aqueous solution is again upward released as droplets through the holes in the second lowermost disc in the organic fluid, and the droplets then disperse in the column of the organic fluid while ascending. Thus, the aqueous solution supplied from the middle of the lower reservoir ascends while repeating fragmentation into droplets and unification of the droplets until it reaches the surface of the column of the organic fluid in the upper reservoir, and there forms a layer of the solution on the organic fluid column and is reserved. The amount of the aqueous solution reserved above the organic fluid column gradually increases as the aqueous solution is further supplied continuously, and after the aqueous solution reaches the drain hole in the upper reservoir, the aqueous solution overflows and is drained from the drain hole. Continuous supply of the organic fluid and the aqueous solution affords continuous counter current contact of the organic fluid and the aqueous solution. The feed rates of the organic fluid and the aqueous solution are adjustable, and the size of droplets of the aqueous solution can be adjusted by varying the rotation speed of the rotating shaft. Washing apparatuses like this are commercially available.

Continuous supply of the liquid product and the aqueous solution to the washing apparatus allows continuous contact of the liquid product and the aqueous solution in the washing apparatus and continuous collection of the refined liquid from the bottom of the washing apparatus. In such a washing process, it is also preferred to continuously supply an aqueous solution of a refining agent to the organic fluid until 0.01 to 5 parts by weight of the refining agent relative to 100 parts by weight of the derivative in the organic fluid, is supplied. Such a washing apparatus is applicable to the process (C") which uses water containing no refining agent.

Thus, in step (C), a refined liquid containing an epihalohydrin, for example, from 70 to 90 wt % as in case of epichlorohydrin is prepared.

In step (D), the epihalohydrin or the 2-methylepihalohydrin and a small amount of other volatile components in the refined liquid thus obtained are removed by evaporation to form a product which is free from these volatile components. The vapor is lead to a condenser and collected as a liquid there.

Concentration of the refined liquid through evaporation of an epihalohydrin or a 2-methylepihalohydrin can be readily performed, for example, by means of an ordinary distillation column, a rotary evaporator, a flash evaporator or a falling film evaporator. However, as the concentration of the epihalohydrin or the 2-methyepihalohydrin come close to 10 wt %, the liquid becomes highly viscous. In particular, when the concentration of the epihalohydrin or the 2-methylepihalohydrin in the liquid becomes below 1 wt %, the evaporation rate of these volatile components decreases suddenly, and therefore, it is difficult to efficiently remove these volatile components. It has been found out that an inadequately refined liquid obtained in step (C) tends to encounter decrease in the content of oxirane oxygen at a high temperature of 100° to 165° C., at a concentration of these volatile components of less than 10 wt %, especially less than 1 wt %. The decrease in the content of oxirane oxygen is thought to be attributable to a trace amount of remaining impurities resulting from insufficient washing in step (C). However, when an aqueous solution which contains an insufficient amount of a refining agent is used, the increased number of washings in step (C) hardly contributes to complete removal of impurities, and unfavorably lowers the yield of the product obtained in step (D). Therefore, it is preferred that an aqueous solution of a refining agent with high refining effect is used for the refining in step (C) in order to obtain a refined liquid containing a tolerably small amount of impurities, and these volatile components are removed from the refined liquid or its concentrate in a short time in step (D) to obtain a product which is substantially free from these volatile components.

It was found that formation of a fluid film thinner than 500 $\mu$m by applying the refined liquid or its concentrate which contains an epihalohydrin or 2-methylepihalohydrin preferably at a concentration of 1 to 60 wt % on a substrate heated to a temperature of from 100° to 165° C. allows those volatile components to evaporate quickly from the film and thereby reduce the concentration of the volatile components in the film. However, it is not effective to form a film thinner than 30 $\mu$m from the refined liquid or its concentrate because the surface area of the film made from a unit weight of the refined liquid or its concentrate increases correspondingly. According to a preferred embodiment of the present invention, a film of 30 to 500 $\mu$m thick, preferably of 100 to 450 $\mu$m thick is formed from the refined liquid or its concentrate by means of a coater on a substrate heated to a temperature of from 100° to 165° C. And by evaporating the above-mentioned volatile components from the film under reduced pressure, preferably under a pressure of the volatile components of at most 5 mmHg, it is possible to reduce the concentration of the volatile components in the film in a short time.

The concentration of volatile components in a fluid film can be reduced to such a level that the film is substantially free from these volatile components, namely to less than 100 ppm by weight, especially to less than 10 ppm by weight through evaporation of the volatile components by continuing heating the film as it is, but also by a more efficient process.

According to a preferred embodiment of the present invention, the volatile components in the refined liquid or its concentrate can be efficiently removed by a process (D') which comprises forming by coating on a surface of a substrate a film of the refined liquid or the concentrate thereof having a thickness of 30 to 500 $\mu$m, preferably 100 to 450 $\mu$m, and having at one end of the film the highest concentration and gradually lowered concentration toward the lowest concentration at the opposite end of the film respectively of the volatile components in the refined liquid or the concentrate thereof, and evaporating from the film the volatile components under a pressure of 5 mmHg or lower, for example, from 0.1 to 5 mmHg, of the components at 100° to 165° C., preferably at 120° to 160° C., while supplying continuously to the end of the film having the highest concentration of the volatile components the refined liquid or the concentrate thereof, conveying gradually toward the opposite end the liquid under the evaporation and the film thickness, and recovering continuously from the opposite end of the film a final liquid having a lowered concentration of the volatile components.

According to the process (D'), it is possible to remove the epihalohydrin, the 2-methylepihalohydrin and other volatile components in the refined liquid obtained in step (C) in a short time to such a level that it is substantially contains no volatile components, and therefore it is possible to remarkably suppress formation of insoluble matters which is likely to occur while it is kept at a high temperature to remove these volatile components. Therefore, a refined liquid containing a large amount of impurities which is obtained by carrying out step (B) and step (C) without using any of the preferred process (B'), the preferred process (C') and the process (C") wherein no refining agent is used, can yield a product containing no insoluble matters by the process (D'). Especially, in the case of production of a product of a crystalline derivative such as the tris(2,3-epoxypropyl)ester or the tris(2-methyl-2,3-epoxypropyl)ester of isocyanuric acid, or the bis(2,3-epoxypropyl)ester or the bis(2-methyl-2,3-epoxypropyl)ester of terephthalic acid, insoluble matters as described above in the product obtained in step (D) can not be removed in subsequent refining step (E). However, if the product obtained in step (D) contains no insoluble matters, a higher purity can be achieved in refining step (E). Therefore, the process (D') is preferable for producing products of these crystalline derivatives.

The preferred process for removing volatile components can be smoothly carried out by means of an evaporator designed for this process. For example, the evaporator comprises a cylinder which is covered with a cap having a liquid inlet and a vapor outlet and has a liquid outlet in the bottom. A jacket is provided around the cylinder to circulate a heating medium, and the cylinder is connected to an evacuator equipped with a condenser through the vapor outlet. In the cylinder, there are a rotating shaft sticking through the cap, a disc fixed to the upper part of the shaft, and a coater below the disc, said coater fitted through a spring to the tip of a holder which is fixed to the shaft, or holded with a clearance in a holder which is fixed to the tip of a bar extending from the shaft. The coater is pressed against the inner wall of the cylinder by a controlled force of the spring or centrifugal force during rotation, and is arranged so that it slides along the inner wall of the cylinder as the rotating shaft rotates. The coater is in the shape of a long rectangular parallelepiped and has a vertically long plane surface facing the cylinder. On the surface from the top to the bottom, a plurality of grooves are cut at a constant interval so as to cross the surface at a constant angle against the horizon. The thickness of a film formed on the inner wall of the cylinder can be adjusted by adjusting the strength of the spring pressing the coater to the inner wall of the evaporator, the feed rate of a refined liquid or its concentrate, the temperature of the film in the evaporator and so on. A refined liquid or its concentrate is supplied through the liquid inlet in the cap onto the disc inside the cylinder, and flows on the disc toward its periphery by centrifugal force as the shaft rotates and reaches the top of the inner wall of the cylinder past the periphery of the disc. It is spread on the inner wall of the cylinder with the plane surface of the coater to form a film on the inner surface of the cylinder. As the refined liquid or its concentrate is continuously supplied, it is mixed with the film on contact at an edge of the plane surface of the coater facing the cylinder while conveyed downward along the inner wall of the cylinder through the inclining grooves. Thus, a refined liquid or its concentrate is continuously supplied as the rotating shaft rotates to form a film throughout the inner wall of the cylinder.

While volatile components are evaporated from the film of the refined liquid or its concentrate, supply of the refined liquid or its concentrate is continued with the rotating shaft rotated. As a result, the film is renewed at the same period as the passage of the coater, and the concentration of volatile components in the film gradually decreases downward so as to be the highest at the top of the inner wall of the cylinder and the lowest at the bottom. As supply of the refined liquid or its concentrate is further continued with rotation of the rotating shaft, the fraction of the film having the lowest concentration of volatile components accumulates on the bottom of the evaporator as a final liquid. The accumulated liquid is recovered through the outlet at the bottom of the evaporator. Evaporators which effect such evaporation are already known and commercially available.

In order to remove volatile components from a refined liquid or its concentrate by means of the above-mentioned evaporator, it is preferred to reduce stepwise the concentration of volatile components, for example, to about 2,000–4,000 ppm at first, and then to such a level that no volatile components are contained in the resulting final liquid, rather than reduce the concentration to 100 ppm or less, especially to 50 ppm or less at one time. When the product is purified by recrystallization as described later, it is not necessary to remove volatile components by evaporation to such a level that the product is substantially free from volatile components, and the product may contain about 1,000 ppm of an epihalohydrin or a 2-methylepihalohydrin.

By step (D), preferred derivatives such as the bis(2,3-epoxypropyl)ester or the bis(2-methl-2,3-epoxypropyl)ester of phthalic acid, isophthalic acid or terephthalic acid; the tris(2,3-epoxypropyl)ester or the tris(2-methyl-2,3-epoxypropyl)ester of trimellitic acid or trimesic acid; the N,N'-bis(2,3-epoxypropyl) derivative or the N,N'-bis(2-methyl-2,3-epoxyrpopyl) derivative of hydantoin; and the tris(2,3-epoxypropyl)ester or the tris(2-methyl-2,3-epoxypropyl)ester of isocyanuric acid are produced as purified products. As described above, in steps (A) to (D), the preferred processes can be used, respectively, and a high purity epoxy compound can be produced by the preferred methods of the present invention which employ these preferred steps (A) to (D) in combination. The preferred methods are a method comprising step (A), step (B) carried out by the process (B'), step (C) carried out by the process (C') and step (D); a method which comprises step (A), step (B) carried out by the process (B'), step (C) and step (D) carried out by the process (D'); a method which comprises step (A), step (B), step (C) carried out by the process (C') and step (D) carried out by the process (D'), and the like. The most preferred method comprises step (A), step (B) carried out by the process (B'), step (C) carried out by the process (C') and step (D) carried out by the process (D'). These preferred methods and the most preferred method are favorable for large-scale industrial production. In particular, in the case of production of crystalline derivatives such as the bis(2,3-epoxypropyl)ester or the bis(2-methyl-2,3-epoxypropyl) ester of terephthalic acid, or the tris(2,3-epoxypropyl)ester or the tris(2-methyl-2,3-epoxypropyl)ester of isocyanuric acid, it is possible to produce these derivatives as high purity products by combining the preferred process (C") which uses no refining agent with these preferred processes. Examples of such a combination are a method wherein after step (A), the process (B') and the process (D') are employed in combination in step (B) and step (D), a method wherein the process (B') and the process (C") which uses no refining agent are used in step (B) and step (C), a method wherein the process (C") which uses no refining agent and the process (D') are employed in combination in step (C) and step (D), respectively, and the most preferred is a method wherein the process (B'), the process (C") which uses no refining agent and the process (D') are employed in combination in steps (B), step (C) and step (D), respectively.

Among the derivatives obtainable in step (D), crystalline compounds such as the bis(2,3-epoxypropyl)ester of terephthalic acid, the bis(2-methyl-2,3-epoxyproyl)ester of terephthalic acid, the tris(2,3-epoxypropyl)ester of isocyanuric acid and the tris(2-methyl-2,3-epoxypropyl)ester of isocyanuric acid can be further purified by recrystallization in step (E) after step (D). In step (E), to dissolve the product recovered in step (D), methanol, ethanol, propanol, methyl ethyl ketone, ethyl acetate, benzene, toluene or a mixture thereof may be used as a solvent, and methanol is particularly preferred. For recrystallization, it is preferable that the product is dissolved in a solvent 1 to 10 times, preferably 2 to 6 times as much by weight as the product at about the boiling temperature of the solvent, and the resulting solution is cooled gradually preferably at a cooling rate of 2° to 30° C./hour to precipitate crystals. The precipitated crystals can be separated from the solution by an ordinary method, for example, by filtration, and the separated crystals are washed with the same solvent, if desired, and then dried by an ordinary method to recover a final product. The final product has a still lower epoxy equivalent and a still higher heat stability than the product before purification by recrystallization. This step (E) is applicable to large-scale industrial production, especially, of a high purity final product, and is carried out next to step (D) irrespective of whether the process (B'), the process (C'), the process (C") or the process (D') is employed.

EXAMPLE 1

Step (A): Into a 2 l glass reaction flask equipped with an agitator having paddle blades, 20 g of water, 5.5 g of tetraethylammonium bromide, 925 g (10 mol) of epichlorohydrin and 166 g (1 mol) of terephthalic acid were put to form a reaction mixture. Then the reaction mixture in the flask was heated under agitation to raise its temperature. When the temperature of the reaction mixture reached 89° C., the reaction mixture started to boil under atmospheric pressure. Heating was continued for 3 hours while the vapor generated was cooled with a condenser with all the liquefied epichlorohydrin continuously returned to the flask and the liquefied water drained out of the flask. When the temperature of the reaction mixture reached 121° C., heating was stopped, and the reaction mixture was cooled to obtain a reaction product at a temperature of 45° C. It was confirmed by liquid chromatography analysis that the reaction product contained no carboxyl groups attributed to the starting material terephthalic acid.

Step (B): Then, dropwise addition of 176 g (2.2 mol in terms of NaOH) of a 50 wt % sodium hydroxide aqueous solution to the whole reaction product in the flask maintained at 45° C. was started under a reduced pressure of 100 mmHg to form a reaction mixture, and at the same time, water and epichlorohydrin were allowed to evaporate from the reaction mixture under vigorous agitation. The degree of vacuum was increased gradually, while the vapor was cooled with a condenser, and all the liquefied epichlorohydrin was continuously returned to the flask, and the liquefied water was drained out of the flask. When the degree of vacuum reached 60 mmHg, the dropwise addition finished, and a slurry containing precipitated sodium chloride was obtained. The dropwise addition took 6 hours. During the addition, the reaction mixture under agitation became turbid due to precipitated sodium chloride, but was maintained uniform throughout. According to liquid chromatography analysis, the slurry thus obtained contained less than 1 wt % of a compound having a 2-hydroxy-3-chloropropyl group.

Step (C): The whole slurry obtained in step (B), 600 g of distilled water and 2 g of sodium toluenesulfonate were agitated in a glass vessel for 5 minutes and then left to stand for 10 minutes. The whole first epichlorohydrin layer was recovered, and the aqueous layer was transferred to another vessel.

Then the whole recovered epichlorohydrin layer, 600 g of a 5 wt % sodium dihydrogenphosphate solution in distilled water and 2 g of sodium toluenesulfonate were agitated in a glass vessel for 5 minutes and left to stand for 10 minutes. The whole second epichlorohydrin layer was recovered, and the aqueous layer was transferred to another vessel.

Then, the whole recovered second epichlorohydrin layer and 800 g of distilled water were agitated in a glass vessel for 5 minutes and allowed to stand for 10 minutes. The whole final epichlorohydrin layer was recovered as refined liquid.

Step (D): The whole final epichlorohydrin layer obtained in Step (C) was introduced to a rotary evaporator, and heated under reduced pressure to remove epichlorohydrin. It was heated at 140° C. under a reduced pressure of 2 mmHg for the last 1 hour before evaporation was stopped. It was cooled to room temperature and the content of the evaporator was recovered to obtain 257 g of a product. The amount of the product was found to correspond to a yield of 92% by calculation, based on the starting material terephthalic acid used in step (A).

In the product, no ionic chlorine was detected, and the product had an epoxide equivalent of 146 and a kaolin turbidity of 1 or less when molten at 140° C., and had an epoxide equivalent of 148 after heated at 150° C. for 24 hours in a sealed vessel. The change in epoxide equivalent upon the heating was found to be 1.4% by calculation.

Step (E): The product obtained in step (D) was 2; molten, and 100 g of the melt was gradually added to 400 g of methanol in a flask under agitation to form a solution of the product in methanol. The solution was heated to the reflux temperature of methanol, and then cooled to 5° C. over 12 hours to precipitate white crystals in the solution. The white crystals were separated by filtration and then dried to obtain 75 g of a final product. The final product had an epoxide equivalent of 140, a kaolin turbidity of 1 or less when molten at 140° C., and an epoxide equivalent of 141 after heated at 150° C. for 24 hours in a sealed vessel, the change in epoxide equivalent by the heating was found to be 0.7% by calculation.

COMPARATIVE EXAMPLE 1

A slurry obtained in the same manner as in step (B) in Example 1 was agitated and then allowed to stand in the same manner as in step (C) in Example 1, but without using sodium toluenesulfonate. Even after 10 minutes of standing, the epichlorohydrin layer was strongly turbid. After another 12 hours of standing, the epichlorohydrin layer was recovered as the first epichlorohydrin layer. The second washing was carried out similarly without using sodium toluenesulfonate, and after 10 minutes of standing, the epichlorohydrin layer was strongly turbid. After another 12 hours of standing, the epichlorohydrin layer was recovered as the second epichlorohydrin layer. The last washing was carried out similarly without using sodium toluenesulfonate, and after 10 minutes of standing, the epichlorohydrin layer was strongly turbid. After another 12 hours of standing, it was recovered as the last epichlorohydrin layer.

The last epichlorohydrin layer was treated in the same manner as in step (D) in Example 1, and 251 g of a product was recovered from the evaporator. The product had an epoxide equivalent of 151, an ionic chlorine content of 5 ppm by weight, a kaolin turbidity of 2 when molten at 140°

C., and an epoxide equivalent of 158 after heated at 150° C. for 24 hours. The change in epoxide equivalent was found to be 4.6% by calculation.

The product was treated in the same manner as in step (E) in Example 1 to obtain 70 g of a dry final product in the form of white crystals. The final product had an epoxide equivalent of 142, a kaolin turbidity of 2 when molten at 140° C., and an epoxide equivalent of 145 after heated at 150° C. for 24 hours in a sealed vessel. The change in epoxide equivalent was found to be 2% by calculation.

EXAMPLE 2

Steps (A) and (B): A slurry containing precipitated sodium chloride was obtained in the same manner as in steps (A) and (B) in Example 1.

Step (C): A final epichlorohydrin layer was recovered in the same manner as in step (C) in Example 1 except that 2 g of sodium vinylsulfonate was used instead of 2 g of sodium toluenesulfonate.

Step (D): The whole final epichlorohydrin layer obtained in step (C) was treated in the same manner as in step (D) in Example 1, and therefore 257 g of a product was recovered from the evaporator. In the product, no ionic chlorine was detected, and the product had an epoxide equivalent of 146, a kaolin turbidity of 1 or less when molten at 140° C., and an epoxide equivalent of 148 after heated at 150° C. for 24 hours in a sealed vessel.

EXAMPLE 3

Steps (A) and (B): A slurry containing precipitated sodium chloride was obtained in the same manner as in steps (A) and (B) in Example 1.

Step (C): A final epichlorohydrin layer was recovered in the same manner as in step (C) in Example 1 except that 2 g of sodium octanesulfonate was used instead of 2 g of sodium toluenesulfonate.

Step (D): The whole final epichlorohydrin layer obtained in step (C) was treated in the same manner as in step (D) in Example 1, and therefore 257 g of a product was recovered from the evaporator. In the product, no ionic chlorine was detected, and had the same epoxide equivalent, the same kaolin turbidity when molten at 140° C. and the same epoxide equivalent after heated at. 150° C. for 24 hours in a sealed vessel, as the product obtained in Example 1.

EXAMPLE 4

Steps (A) and (B): A slurry containing precipitated sodium chloride was obtained in the same manner as in steps (A) and (B) in Example 1.

Step (C): A final epichlorohydrin layer was recovered in the same manner as in step (C) in Example 1 except that 2 g of ammonium toluenesulfonate was used instead of 2 g of sodium toluenesulfonate.

Step (D): The whole final epichlorohydrin layer obtained in step (C) was treated in the same manner as in step (D) in Example 1, and therefore 256 g of a product was recovered from the evaporator. In the product, no ionic chlorine was detected, and the product had an epoxide equivalent of 147, a kaolin turbidity of 1 or less when molten at 140° C. and an epoxide equivalent of 150 after heated at 150° C. for 24 hours in a sealed vessel. The change in epoxide equivalent was found to be 2% by calculation.

EXAMPLE 5

Steps (A) and (B): Step (A) in Example 1 was reproduced except that 1,065 g of 2-methylepichlorohydrin was substituted for 925 g of epichlorohydrin. When the temperature of the reaction mixture reached 95° C., reflux of 2-methylepichlorohydrin was started. The reaction mixture was heated eventually to 120° C. over 8 hours. 176 g of a 50 wt % sodium hydroxide aqueous solution was added to the reaction mixture maintained at 45° C. over 6 hours in the same manner as in step (B) in Example 1 to obtain a slurry containing precipitated sodium chloride.

Step (C): The whole slurry obtained in step (B) was treated in the same manner as in step (C) in Example 1 except that 2 g of potassium benzenesulfonate was used instead of 2 g of sodium toluenesulfonate, and the final 2-methylepichlorohydrin layer was recovered.

Step (D): The whole final 2-methylepichlorohydrin layer obtained in step (C) was treated in the same manner as in step (D) in Example 1, and 284 g of a product was recovered from the evaporator. In the product, no ionic chlorine was detected, and the product had an epoxide equivalent of 163, a kaolin turbidity of 1 or less when molten at 140° C., and an epoxide equivalent of 165 after heated at 150° C. for 24 hours in a sealed vessel. The change in epoxide equivalent was found to be 1.2% by calculation.

EXAMPLE 6

Step (A): Into a 2 l glass reaction flask equipped with an agitator having paddle blades, 30 g of water, 5.5 g of tetramethylammonium chloride, 1,388 g (15 mol) of epichlorohydrin and 129 g (1 mol) of cyanuric acid were put to form a reaction mixture. Then the reaction mixture in the flask was heated under agitation to raise its temperature. When the temperature of the reaction mixture reached 89° C., the reaction mixture started to boil under atmospheric pressure. Heating was continued for 5 hours while the vapor generated was cooled with a condenser with all the liquefied epichlorohydrin continuously returned to the flask and the liquefied water drained out of the flask. When the temperature of the reaction mixture reached 120° C., heating was stopped, and the reaction mixture was cooled to obtain a reaction product at a temperature of 45° C. In the product, unreacted cyanuric acid was not detected.

Step (B): Then, dropwise addition of 256 g (3.2 mol in terms of NaOH) of a 50 wt % sodium hydroxide aqueous solution to the whole reaction product in the flask maintained at 50° C. was started under a reduced pressure of 100 mmHg to form a reaction mixture, and at the same time, water and epichlorohydrin were allowed to evaporate from the reaction mixture under vigorous agitation. The degree of vacuum was increased gradually, while the vapor was cooled with a condenser, and all the liquefied epichlorohydrin was continuously returned to the flask, and the liquefied water was drained out of the flask. When the degree of vacuum reached 60 mmHg, the dropwise addition finished, and a slurry containing precipitated sodium chloride was obtained. The dropwise addition took 6 hours. During the addition, the reaction mixture under agitation became turbid due to precipitated sodium chloride, but was maintained uniform throughout. According to liquid chromatography analysis, the slurry thus obtained contained less than 1 wt % of a compound having a 2-hydroxy-3-chloropropyl group.

Step (C): The whole slurry obtained in step (B), 600 g of distilled water and 2 g of sodium toluenesulfonate were agitated in a glass vessel for 5 minutes and then left to stand for 10 minutes. The whole first epichlorohydrin layer was recovered, and the aqueous layer was transferred to another vessel.

Then the whole recovered epichlorohydrin layer, 600 g of a 5 wt % sodium dihydrogenphosphate solution in distilled water and 2 g of sodium toluenesulfonate were agitated in a glass vessel for 5 minutes and left to stand for 10 minutes. The whole second epichlorohydrin layer was recovered, and the aqueous layer was transferred to another vessel.

Then, the whole recovered second epichlorohydrin layer and 800 g of distilled water were agitated in a glass vessel for 5 minutes and allowed to stand for 10 minutes. The whole final epichlorohydrin layer was recovered.

Step (D); The whole final epichlorohydrin layer obtained in Step (C) was introduced to a rotary evaporator, and heated under reduced pressure to remove epichlorohydrin. It was heated at 140° C. under a reduced pressure of 2 mmHg for the last 1 hour before evaporation was stopped. It was cooled to room temperature and the content of the evaporator was recovered to obtain 267 g of a product. The amount of the product was found to correspond to a yield of 90% by calculation, based on the starting material cyanuric acid used in step (A).

In the product, no ionic chlorine was detected, and the product had an epoxide equivalent of 103 and a kaolin turbidity of 1 or less when molten at 140° C., and had an epoxide equivalent of 104 after heated at 150° C. for 24 hours in a sealed vessel. The change in epoxide equivalent upon the heating was found to be 1% by calculation.

Step (E): The product obtained in step (D) was molten, and 100 g of the melt was gradually added to 400 g of methanol in a flask under agitation to form a solution of the product in methanol. The solution was heated to the reflux temperature of methanol, and then cooled to 5° C. over 12 hours to precipitate white crystals in the solution. The white crystals were separated by filtration and then dried to obtain 82 g of a final product.

The final product had an epoxide equivalent of 99, a kaolin turbidity of 1 or less when molten at 140° C., and an epoxide equivalent of 99 after heated at 150° C. for 24 hours in a sealed vessel, the change in epoxide equivalent by the heating was found to be 0% by calculation.

COMPARATIVE EXAMPLE 2

A slurry obtained in the same manner as in step (B) in Example 6 was allowed to stand in the same manner as in step (C) in Example 6, but without using sodium toluene-sulfonate. Even after 10 minutes of standing, the epichlorohydrin layer was strongly turbid. After another 12 hours of standing, the epichlorohydrin layer was recovered as the first epichlorohydrin layer. The second washing was carried out similarly without using sodium toluenesulfonate, and after 10 minutes of standing, the epichlorohydrin layer was strongly turbid. Another 12 hours of standing, the epichlorohydrin layer was recovered as the second epichlorohydrin layer. The last washing was carried out similarly without using sodium toluenesulfonate, and after 10 minutes of standing, the epichlorohydrin layer was strongly turbid. After another 12 hours of standing, it was recovered as the last epichlorohydrin layer.

The last epichlorohydrin layer was treated in the same manner as in step (D) in Example 6, and 258 g of a product was recovered from the evaporator. The product had an epoxide equivalent of 108, an ionic chlorine content of 4 ppm by weight, a kaolin turbidity of 3 when molten at 140° C., and an epoxide equivalent of 113 after heated at 150° C. for 24 hours. The change in epoxide equivalent was found to be 4.6% by calculation.

The product was treated in the same manner as in step (E) in Example 6 to obtain 80 g of a dry final product in the form of white crystals. The final product had an epoxide equivalent of 100, a kaolin turbidity of 2 when molten at 140° C., and an epoxide equivalent of 101 after heated at 150° C. for 24 hours in a sealed vessel. The change in epoxide equivalent was found to be 1% by calculation.

EXAMPLE 7

Step (A) and (B): A slurry containing precipitated sodium chloride was prepared in the same manner as in steps (A) and (B) in Example 6 except that 5.5 g of ethyltriph-enylphosphonium bromide was used instead of 5.5 g of tetramethylammonium chloride.

Step (C): A final epichlorohydrin layer was recovered in the same manner as in step (C) in Example 6.

Step (D): The whole final epichlorohydrin layer obtained in step (C) was treated in the same manner as in step (D) in Example 6 to recover 265 g of a product from the evaporator. In the product, no ionic chorine was detected, and the product had an epoxide equivalent of 104, a kaolin turbidity of 1 or less when molten at 140° C., and an epoxide equivalent of 105 after heated at 150° C. for 24 hours in a sealed vessel. The change in epoxide equivalent was found to be 1% by calculation.

EXAMPLE 8

Steps (A) and (B): A slurry containing precipitated sodium chloride was obtained in the same manner as in steps (A) and (B) in Example 1.

Step (C): A final epichlorohydrin layer was recovered in the same manner as in step (C) in Example 1 except that 2 g of toluenesulfonic acid was used instead of 2 g of sodium toluenesulfonate.

Step (D): The whole final epichlorohydrin layer obtained in step (C) was treated in the same manner as in step (D) in Example 1, and therefore 255 g of a product was recovered from the evaporator. In the product, no ionic chlorine was detected, and the product had an epoxide equivalent of 146, a kaolin turbidity of 1 or less when molten at 140° C. and an epoxide equivalent of 148 after heated at 150° C. for 24 hours in a sealed vessel. The change in epoxide equivalent was found to be 1.4% by calculation.

EXAMPLE 9

Steps (A) and (B): A slurry containing precipitated sodium chloride was obtained in the same manner as in steps (A) and (B) in Example 1.

Step (C): A final epichlorohydrin layer was recovered in the same manner as in step (C) in Example 1 except that 2 g of sodium benzoate was used instead of 2 g of sodium toluenesulfonate.

Step (D): The whole final epichlorohydrin layer obtained in step (C) was treated in the same manner as in step (D) in Example 1, and therefore 258 g of a product was recovered from the evaporator. In the product, no ionic chlorine was detected, and the product had an epoxide equivalent of 147, a kaolin turbidity of 1 or less when molten at 140° C. and an epoxide equivalent of 150 after heated at 150° C. for 24 hours in a sealed vessel. The change in epoxide equivalent was found to be 2% by calculation.

EXAMPLE 10

Steps (A) and (B): A slurry containing crystallized sodium chloride was obtained in the same manner as in steps (A) and (B) in Example 1.

Step (C): A final epichlorohydrin layer was recovered in the same manner as in step (C) in Example 1 except that 2 g of the triethanolamine salt of toluenesulfonic acid was used instead of 2 g of sodium toluenesulfonate.

Step (D): The whole final epichlorohydrin layer obtained in step (C) was treated in the same manner as in step (D) in Example 1, and therefore 256 g of a product was recovered from the evaporator. In the product, no ionic chlorine was detected, and the product had an epoxide equivalent of 147, a kaolin turbidity of 1 or less when molten at 140° C. and an epoxide equivalent of 149 after heated at 150° C. for 24 hours in a sealed vessel. The change in epoxide equivalent was found to be 1.4% by calculation.

EXAMPLE 11

The scale of Example 1 was enlarged by 10 times by using a 20 l glass reaction vessel equipped with an agitator having paddle blades.

Step (A) could be carried out smoothly in the same manner as in Example 1.

Step (B) was carried out in the same manner as in Example 1, but in the course of addition of a sodium hydroxide aqueous solution, a part of the precipitated sodium chloride started to accumulate on the side wall near the bottom of the reactor. As the sodium hydroxide aqueous solution was further added, precipitated sodium chloride accumulated more and more and adhered to the side wall of the reactor. The addition of sodium hydroxide was continued while the agitator was rotated at an increased rotation speed, but the sodium hydroxide on the wall did not disperse in the reaction mixture to the end of the addition. The resulting slurry contained less than 1 wt % of a compound having a 2-hydroxy-3-chloropropyl group. Step (C) was carried out smoothly in the same manner as in Example 1.

Step (D) was conducted on the same scale in the same manner as in Example 1 smoothly, but the yield slightly decreased to 90%. The product had an epoxide equivalent of 151, a kaolin turbidity of 1 or less when molten at 140° C., and an epoxide equivalent of 155 after heated at 150° C. for 24 hours in a sealed vessel. The change in epoxide equivalent by heating was found to be 2.6% by calculation.

Step (E) was carried out on the same scale in the same manner as in Example 1, but the yield of the resulting final product slightly decreased to 72%. The final product had an epoxide equivalent of 140, and an epoxide equivalent of 141 after heated at 150° C. for 24 hours in a sealed vessel.

EXAMPLE 12

Example 11 was reproduced by using a reactor equipped with two baffles of 15 cm long, 2 cm wide and 2 mm thick, instead.

Step (A) was carried out smoothly in the same manner as in Example 11. In step (B), the reaction mixture was maintained uniform by agitation without accumulation of precipitated sodium chloride or its adhesion to the side wall, unlike Example 11. Steps (C) and (D) were carried out in the same manner as in Example 11 to obtain a product in a yield of 93%. The product had an epoxide equivalent of 146, a kaolin turbidity of 1 or less when molten at 140° C., and an epoxide equivalent of 148 after heated at 150° C. for 24 hours in a sealed vessel. The change in epoxide equivalent by the heating was found to be 1.4% by calculation. Step (E) was carried out in the lo same manner as in Example 11 to obtain a product in a yield of 75%.

EXAMPLE 13

The scale of Example 6 was enlarged by 100 times.

The reactor used was made of stainless steel, had an internal volume of 200 l, and had two baffles of 60 cm long, 4 cm wide and 4 mm thick inside. The agitator used comprised a rotating shaft and two plane blades fixed to the shaft. The two plane blades were arranged symmetrically in respect of the rotating shaft on a plane containing the shaft, and the upper two-thirds of blades were made of lattices, and the lower one-third were paddles. The width of the agitator was 0.53 time the inner diameter of the reactor.

When the reactor is sunk and rotated in a liquid in the reactor, the paddles on the lower parts impel the liquid on the bottom of the reactor to flow toward the lower parts of the side wall and form a laminar circulating stream which ascends along the side wall of the reactor, to the surface of the liquid and turns downward at the surface of the liquid and swirls downward while being sheared into fragments by the lattices of the rotating agitator. Therefore, when the agitator is rotated continuously, the liquid is maintained uniform under agitation which causes the liquid to produce a stream circulating and ascending along the inner side wall from the bottom of the reactor to the surface of the slurry, turning there the ascending stream to a stream swirling downward and shearing across the swirling stream into fragments.

Step (A) was carried out smoothly in the same manner as in Example 6. In step (B), the reaction mixture was maintained uniform without accumulation of precipitated sodium chloride or its adhesion to the side wall of the reactor, unlike Example 11. Step (C) was carried out in the same manner as in Example 6. Step (D) was carried out on the same scale as in Example 6 to obtain a product in a yield of 90%. The product had an epoxide equivalent of 102, a kaolin turbidity of 1 or less when molten at 140° C., and an epoxide equivalent of 103 after heated at 150° C. for 24 hours in a sealed vessel. The change in epoxide equivalent by the heating was found to be 1% by calculation. Step (E) was carried out on the same scale in the same manner as in Example 6 to obtain a product in a yield of 82%. The product had an epoxide equivalent of 99, and had the same epoxide equivalent even after heated at 150° C. for 24 hours in a sealed vessel.

EXAMPLE 14

Step (A): Into a 20 l glass reaction flask equipped with an agitator having paddle blades, 300 g of water, 55 g of tetramethylammonium chloride, 13.88 kg (150 mol) of epichlorohydrin and 1.29 kg (10 mol) of cyanuric acid were put to form a reaction mixture. Then the reaction mixture in the flask was heated under agitation to raise its temperature.

When the temperature of the reaction mixture reached 89° C., the reaction mixture started to boil under atmospheric pressure. Heating was continued for 5 hours while the vapor generated was cooled with a condenser with all the liquefied epichlorohydrin continuously returned to the flask and the liquefied water drained out of the flask. When the temperature of the reaction mixture reached 120° C., heating was stopped, and the reaction mixture was cooled to obtain a reaction product at a temperature of 45° C. In the product, unreacted cyanuric acid was not detected.

Step (B): Then, dropwise addition of 2.56 kg (3.2 mol in terms of NaOH) of a 50 wt % sodium hydroxide aqueous solution to the whole reaction product maintained at 50° C. was started under a reduced pressure of 100 mmHg to form a reaction mixture, and at the same time, water and epichlorohydrin were allowed to evaporate from the reaction mixture under vigorous agitation.

The degree of vacuum was increased gradually, while the vapor was cooled with a condenser, and all the liquefied epichlorohydrin was continuously returned, and the liquefied water was drained out of the reactor. When the degree of vacuum reached 60 mmHg, the dropwise addition finished, and a slurry containing precipitated sodium chloride was obtained. The dropwise addition took 6 hours. After another 5 minutes of reflux, the vacuum in the reactor was released, and the agitation was stopped.

According to liquid chromatography analysis, the slurry thus obtained contained less than 1 wt % of a compound having a 2-hydroxy-3-chloropropyl group.

Steps (A) and (B) were repeated 4 times, and the whole slurry thus obtained was used for step (C).

Step (C): The above slurry was gently agitated in a vessel together with 24 l of distilled water and 80 g of sodium toluenesulfonate to dissolve the precipitated sodium chloride in the slurry in the water added, and the liquid in the vessel was allowed to stand, and then the whole organic layer was recovered to obtain a transparent liquid product.

A washing apparatus was arranged for washing the liquid product with droplets. The washing apparatus comprised a glass main cylinder having a height of 300 mm and an inner diameter of 50 mm, a cylindrical reservoir connected above to the upper end of the main cylinder, another cylindrical reservoir connected below to the lower end of the main cylinder, a cap covering the upper reservoir, and a rotating shaft extending to the lower end of the main cylinder through the center of the cap. The upper reservoir had almost the same inner diameter as the main cylinder, a height of 160 mm and a drain hole in its upper part. Through the cap, there was equipped a liquid supply pipe extending nearly to the lower end of the upper reservoir. The lower reservoir had almost the same inner diameter and a depth of 160 mm and a drain hole at the bottom. At the middle of the lower reservoir, there was a liquid supply pipe extending nearly to the lower end of the rotating shaft through its side wall. Around the rotating shaft, six discs having many holes were provided at a constant interval from the lower end of the shaft about to the upper end of the main cylinder. On the inner side wall of the main cylinder, there were doughnut baffles of 15 mm wide each interposed between the every disc. Each disc was 40 mm in diameter, and a hoop ring was fitted underneath the periphery of each disc. Holes having a 2 mm diameter were opened in each disc through it from the upper surface to the lower surface. The rotating shaft rotated reciprocally, when driven by a driving system connected to its top end.

The liquid product was introduced into the washing apparatus until the upper reservoir was filled half, and the rotating shaft was rotated at a speed of 110 cycles per minute. An aqueous solution containing 0.33 wt % of sodium toluenesulfonate and 3 wt % of sodium dihydrogenphosphate was supplied at a feed rate of 0.078 l/min, and after the aqueous solution which had been brought into contact with the liquid product started draining through the drain hole of the upper reservoir, the liquid product was drained from the bottom of the lower reservoir, and the unrefined liquid product was supplied through the liquid supply pipe on the upper part of the washing apparatus at a rate of 0.51 l/min. The liquid product recovered soon after the start of draining was returned to a storage tank for the liquid product, because it is not refined yet. It was observed that the supplied aqueous solution was dispersed in the epichlorohydrin layer, forming droplets of about 0.3 to 7 mm in size. After a refined transparent liquid started draining, 20 l of the drained liquid was collected as a refined liquid.

Next, the refined liquid was washed with a 0.03 wt % sodium toluenesulfonate aqueous solution. The refined liquid and the aqueous solution were supplied continuously at feed rate of 0.45 l/min and 0.19 l/min, respectively, while the rotating shaft was rotated at a speed of 110 cycles/min to obtain a second transparent liquid. The epichlorohydrin layer obtained in the second washing was collected as the refined liquid refined by step (C). The refined liquid contained 83 wt % of epichlorohydrin.

Step (D): A 2 l portion of the refined liquid collected in step (C) was introduced to a 10 l rotary evaporator. Evaporation of epichlorohydrin was started under reduced pressure at a temperature of 60° C., and the evaporation was continued while the degree of vacuum was gradually decreased to 2 mmHg and the temperature was raised to 140° C. The product obtained by cooling the liquid had an epoxide equivalent of 102.

EXAMPLE 15

Steps (A) to (C) in Example 6 were conducted on a scale enlarged by 10 times.

Step (D): The refined liquid collected in step (C) was treated in a flash evaporator to obtain a concentrate having an epichlorohydrin concentration of 70 wt %. From the refined liquid, epichlorohydrin was removed by evaporation by means of a film evaporator to obtain a product of triglycidyl isocyanurate having a lowered epichlorohydrin concentration.

The evaporator used comprised a cylinder of 315 mm in diameter and 735 mm in height which was covered with a cap having a liquid inlet and a vapor outlet and had a liquid outlet in the bottom. A jacket was provided around the cylinder to circulate a heating medium, and the cylinder was connected to an evacuator equipped with a condenser through the vapor outlet. In the cylinder, there were a rotating shaft sticking through the cap, a disc of 275 mm in diameter fixed to the upper part of the shaft, and a coater below the disc, the coater being holded with a clearance in a holder which is fixed to the tip of a bar extending from the shaft. The coater was arranged so as to be pressed against the inner wall of the cylinder by centrifugal force and slide along the inner wall of the cylinder as the rotating shaft rotated. The coater was in the shape of a 600 mm-long rectangular parallelepiped and had a vertically long 20 mm-wide plane surface facing the cylinder. On the plane surface from the top to the bottom, a plurality of grooves were cut at a 12 mm interval so as to cross the surface at an angle of 45° against the horizon. The grooves were 8 mm deep and 12 mm wide.

Heating steam was introduced into the jacket of the evaporator, the rotating shaft was rotated at a speed of 200 rpm, and the evacuator was operated to maintain a reduced pressure of 10 mmHg. The concentrate of the liquid product having an epichlorohydrin concentration of 70 wt % was supplied to the evaporator at a rate of 22.4 kg/h with a film thickness of 230 μm and an average retention time of 15 seconds, a product having a temperature of 123° C. and an epoxide equivalent of 103 and containing 2,500 ppm of epichlorohydrin was collected from the outlet in the bottom of the evaporator.

The product thus obtained was a transparent liquid containing no insoluble matters. The liquid product thus obtained was treated again in the evaporator to obtain a product having a still lower epihalohydrin concentration.

In the second run, heating steam was introduced in the jacket, the rotating shaft was rotated at 200 rpm, and the evacuator was operated to maintain a reduced pressure of 0.2 mmHg. The above liquid having an epichlorohydrin concentration of 2,500 ppm was supplied at a rate of 14.0 kg/h with a film thickness of 170 μm and an average retention time of 18 seconds, and a product having a temperature of 155° C., an epoxide equivalent of 103 and containing epichlorohydrin 54 ppm was recovered from the outlet in the bottom of the evaporator. The recovered product was a transparent liquid containing no insoluble matters. The yield of triglycidyl isocyanurate was 90%, based on the starting material isocyanuric acid.

Step (E): 100 g of the melt of the product having an epichlorohydrin concentration of 54 ppm obtained in step (D) was gradually added to 400 g of methanol in a flask under agitation to form a solution of the product in methanol. The solution was heated to the reflux temperature of methanol, and then cooled to 5° C. over 12 hours to precipitate white crystals in the solution. The white crystals were separated by filtration and then dried to obtain 82 g of a final product having an epoxide equivalent of 99.

EXAMPLE 16

A slurry containing precipitated sodium chloride was obtained in the same manner as in steps (A) and (B) in Example 13.

Then, the whole slurry was treated in the same manner as in step (C) in Example 14 at an increased rate. The precipitated sodium chloride was removed from the slurry by dissolution to obtain a liquid product, and the liquid product was washed by means of the washing apparatus firstly with an aqueous solution of sodium toluenesulfonate and sodium hydrogenphosphate, and then with an aqueous solution of sodium toluenesulfonate to obtain a refined liquid. The refined liquid was concentrated by means of a flash evaporator to obtain a concentrate, and epichlorohydrin was removed by means of the film evaporator in the same manner as in step (D) in Example 15 to obtain 27.0 kg of a product having an epoxide equivalent of 101 and an epichlorohydrin concentration of 80 ppm.

EXAMPLE 17

Steps (A) and (B): A slurry containing precipitated sodium chloride was prepared in the same manner as in steps (A) and (B) in Example 1.

Step (C): The slurry was washed with distilled water at the first time in the same manner as in Example 1 without using a refined agent. The second washing was conducted in the same manner as in Example 1 except that 2 g of sodium cinnamate was used instead of 2 g of sodium toluenesulfonate.

The last washing was conducted in the same manner as in Example 1 except that an aqueous solution of 0.1 g of sodium cinnamate in 800 g of distilled water was used to obtain a refined liquid.

Step (D): The whole final epichlorohydrin layer obtained in step (C) was treated in the same manner as in step (D) in Example 1, and therefore 257 g of a product was recovered from the evaporator. In the product, no ionic chlorine was detected, and the product had the same epoxide equivalent, the same kaolin turbidity when molten at 140° C. and the same epoxide equivalent after heated at 150° C. for 24 hours in a sealed vessel, as the product obtained in Example 1.

EXAMPLE 18

Steps (A) and (B): A slurry containing precipitated sodium chloride was prepared in the same manner as in steps (A) and (B) in Example 1.

Step (C): The slurry was washed with distilled water at the first time in the same manner as in Example 1 without using a refined agent.

The second washing was conducted in the same manner as in Example 1 except that 2 g of a formaldehyde condensate of sodium naphthalenesulfonate known as a water-soluble water reducing agent was used instead of 2 g of sodium toluenesulfonate.

The last washing was conducted in the same manner as in Example 1 except that an aqueous solution of 0.1 g of a formaldehyde condensate of sodium naphthalenesulfonate in 800 g of distilled water was used to obtain a refined liquid.

Step (D): The whole final epichlorohydrin layer obtained in step (C) was treated in the same manner as in step (D) in Example 1, and therefore 257 g of a product was recovered from the evaporator. In the product, no ionic chlorine was detected, and the product had the same epoxide equivalent, the same kaolin turbidity when molten at 140° C. and the same epoxide equivalent after heated at 150° C. for 24 hours in a sealed vessel, as the product obtained in Example 1.

EXAMPLE 19

Steps (A) and (B): A slurry containing precipitated sodium chloride was prepared in the same manner as in steps (A) and (B) in Example 1.

Step (C): The first washing was conducted in the same manner as in Example 1 except that 0.1 g of disodium phthalate was used instead of 2 g of sodium toluenesulfonate.

The second washing was conducted in the same manner as in Example 1except that 0.5 g of disodium phthalate was used instead of 2 g of sodium toluenesulfonate.

The last washing was conducted in the same manner as in Example 1 except that an aqueous solution of 0.1 g of disodium phthalate in 800 g of distilled water was used to obtain a refined liquid.

Step (D): The whole final epichlorohydrin layer obtained in step (C) was treated in the same manner as in step (D) in Example 1, and therefore 257 g of a product was recovered from the evaporator. In the product, no ionic chlorine was detected, and the product had the same epoxide equivalent, the same kaolin turbidity when molten at 140° C. and the same epoxide equivalent after heated at 150° C. for 24 hours in a sealed vessel, as the product obtained in Example 1.

EXAMPLE 20

Steps (A) and (B): A slurry containing precipitated sodium chloride was prepared in the same manner as in steps (A) and (B) in Example 1.

Step (C): The first washing was conducted in the same manner as in Example 1 except that 0.2 g of disodium salicylate was used instead of 2 g of sodium toluenesulfonate.

The second washing was conducted in the same manner as in Example 1 except that 0.5 g of disodium salicylate was used instead of 2 g of sodium toluenesulfonate.

The last washing was conducted in the same manner as in Example 1 to obtain a refined liquid.

Step (D): The whole final epichlorohydrin layer obtained in step (C) was treated in the same manner as in step (D) in Example 1, and therefore 257 g of a product was recovered from the evaporator. In the product, no ionic chlorine was detected, and the product had the same epoxide equivalent, the same kaolin turbidity when molten at 140° C. and the same epoxide equivalent after heated at 150° C. for 24 hours in a sealed vessel, as the product obtained in Example 1.

EXAMPLE 21

Steps (A) and (B): A slurry containing precipitated sodium chloride was prepared in the same manner as in steps (A) and (B) in Example 1.

Step (C): The slurry was washed with distilled water at the first time in the same manner as in Example 1 without using a refined agent.

The second washing was conducted in the same manner as in Example 1 except that 2 g of sodium laurylsulfate was used instead of 2 g of sodium toluenesulfonate.

The last washing was conducted in the same manner as in Example 1 except that an aqueous solution of 0.2 g of sodium laurylsulfate in 800 g of distilled water was used to obtain a refined liquid.

Step (D): The whole final epichlorohydrin layer obtained in step (C) was treated in the same manner as in step (D) in Example 1, and therefore 257 g of a product was recovered from the evaporator. In the product, no ionic chlorine was detected, and the product had the same epoxide equivalent, the same kaolin turbidity when molten at 140° C. and the same epoxide equivalent after heated at 150° C. for 24 hours in a sealed vessel, as the product obtained in Example 1.

EXAMPLE 22

Example 11 wherein terephthalic acid was used as the starting material was reproduced on a scale enlarged by 10 times by using the reactor used in Example 13 in steps (A) and (B), the washing apparatus used in Example 14 in step (C) and the film evaporator used in Example 15 in step (D).

Step (A) could be carried out smoothly in the same manner as in Example 11. Step (B) was carried out without accumulation of precipitated sodium chloride or its adhesion to the side wall of the reactor, unlike Example 11, and the reaction mixture was maintained uniform throughout. The finished reaction mixture was recovered as a slurry.

Step (C) was carried out without using a refining agent. After addition of 60 kg of distilled water, the whole slurry was gently agitated in a vessel to dissolve the precipitated sodium chloride in the slurry in the added water, and allowed to stand for 12 hours. The whole organic layer was recovered to obtain a transparent liquid product. The liquid product was washed with distilled water at the first time in the same manner as in Example 14 by supplying the transparent liquid product and washing distilled water to the washing apparatus to obtain a transparent refined liquid. The recovered liquid was washed with distilled water again to obtain a refined liquid by step (C).

Step (D) was carried out in the same manner as in Example 15. The refined liquid was firstly treated in a flash evaporator to obtain a concentrate having an epichlorohydrin concentration of 70 wt %, and the concentrate was supplied to the evaporator, and treated at the first time under an average reduced pressure of 10 mmHg with a film thickness of 220 μm and an average retention time of 15 seconds to obtain a product having an epichlorohydrin content of 2,600 ppm at 120° C. from the outlet in the bottom of the evaporator, and at the second time under an average reduced pressure of 0.2 mmHg with a film thickness of 180 μm and an average retention time of 18 seconds, to obtain 25.8 kg of a product having an epichlorohydrin content of 60 ppm at 155° C. from the outlet in the bottom of the evaporator.

The product thus obtained had an epoxide equivalent of 146 and was a transparent liquid containing no insoluble matters.

EXAMPLE 23

Steps (A) and (B) were carried out by using the reactor used in Example 13, and step (D) was carried out by using the film evaporator used in Example 15.

Step (A): 1,000 g of water, 250 g of sodium bromide as a catalyst, 92.5 kg of epichlorohydrin and 8.3 kg of terephthalic acid were mixed to form a reaction mixture. The reaction mixture was heated to 120° C. over 12 hours under reflux while liquefied epichlorohydrin was returned to the reactor and liquefied water was drained out of the reactor. The reaction mixture started boiling at 90° C. under atmospheric pressure. When the temperature of the reaction mixture reached 120° C., heating was stopped and then followed by cooling to 45° C. to obtain a reaction product.

Step (B): To the whole reaction product maintained at 45° C., 8.8 kg of a 50 wt % sodium chloride aqueous solution was added dropwise over 6 hours under agitation, while water and epichlorohydrin were evaporated from the resulting reaction mixture so that epichlorohydrin was refluxed and water was drained out of the reactor. The addition was started at a reduced pressure of 100 mmHg, and the degree of vacuum was increased gradually. During do the addition, the reaction mixture under agitation became turbid due to precipitated sodium chloride, but was maintained uniform throughout. Thus, a final slurry was obtained without accumulation of precipitated sodium chloride or its adhesion to the side wall of the reactor.

Step (C): After addition of 3 kg of distilled water, the whole slurry was gently agitated in a vessel and allowed to stand for 12 hours. The organic layer was recovered in the form of a transparent liquid in which precipitated sodium chloride was not contained. Then to the whole transparent liquid, 3 kg of a 5 wt % sodium dihydrogenphosphate aqueous solution was added, and the resulting mixture was agitated and then allowed to stand for 6 hours. The organic layer was recovered in the form of a refined transparent liquid. 3 kg of distilled water was added to the whole transparent liquid again and the mixture was agitated and allowed to stand for 6 hours. The organic layer was recovered as a refined transparent liquid. It is thought that the fact the transparent organic layer was obtained in the above washing by using water without using a refining agent was attributable to the catalyst used in step (A).

Step (D) was carried out in the same manner as in Example 15. The refined liquid was firstly treated in a flash evaporator to obtain a concentrate having an epichlorohydrin concentration of 70 wt %, and the concentrate was supplied to the evaporator, and treated at the first time under an average reduced pressure of 10 mmlg with a film thickness of 225 μm and an average retention time of 16 seconds to obtain a product having an epichlorohydrin content of 2,400 ppm at 120° C. from the outlet in the bottom of the evaporator, and at the second time under an average reduced pressure of 0.2 mmHg with a film thickness of 175 μm and an average retention time of 20 seconds, to obtain 11.4 kg of a product having an epichlorohydrin content of 50 ppm at 155° C. from the outlet in the bottom of the evaporator.

The product thus obtained had an epoxide equivalent of 153 and was a transparent liquid containing no insoluble matters.

EXAMPLE 24

Step (A): The same reactor equipped with an agitator as used in Example 13 was arranged. 3 kg of water, 550 g of tetramethylammonium chloride, 138.8 kg of epichlorohydrin and 12.9 kg of cyanuric acid were put in the reactor and agitated to form a reaction mixture. Then, the reaction mixture was heated under agitation to raise the temperature.

When the temperature of the reaction mixture reached 89° C., the reaction mixture started to boil under atmospheric pressure. Heating was continued for 5 hours while the vapor generated was cooled with a condenser with all the liquefied epichlorohydrin continuously returned to the reactor and the liquefied water drained out of the reactor. When the temperature of the reaction mixture reached 120° C., heating was stopped, and the reaction mixture was cooled to obtain a reaction product at a temperature of 45° C. It was confirmed that the reaction product contained no unreacted cyanuric acid.

Step (B): Then, dropwise addition of 25.6 kg of a 50 wt % sodium hydroxide aqueous solution to the whole reaction product maintained at 50° C. was started under a reduced pressure of 100 mmHg to form a reaction mixture, and at the same time, water and epichlorohydrin were evaporated from the reaction mixture.

The degree of vacuum was increased gradually, while the vapor was cooled with a condenser, the liquefied epichlorohydrin was continuously returned to the reactor, and the liquefied water was drained out of the reactor. When the degree of vacuum reached 60 mmg, the dropwise addition finished, and a slurry containing precipitated sodium chloride was obtained. The dropwise addition took 6 hours. During the addition, the reaction mixture under agitation became turbid due to precipitated sodium chloride, but was maintained uniform throughout. The reflux was continued for another 5 minutes and then the vacuum in the reactor was released, and the agitation was stopped.

According to liquid chromatography analysis, the slurry thus obtained contained less than 1 wt % of a compound having a 2-hydroxy-3-chloropropyl group.

Step (C): The whole slurry obtained in step (B) was washed three times. Firstly, it was agitated with 90 kg of water and then allowed to stand for 24 hours. Secondly, it was agitated with 15 kg of 5 wt % sodium dihydrogenphosphate aqueous solution and then allowed to stand 24 hours. Finally, it was agitated with 90 kg of water and then allowed to stand for 24 hours. The final epichlorohydrin layer was recovered as a refined liquid.

Step (D): The whole final epichlorohydrin layer obtained in Step (C) was introduced to a rotary evaporator by portions and heated under reduced pressure to remove epichlorohydrin. It was heated at 140° C. under a reduced pressure of 2 mmHg for the last 1 hour before evaporation was stopped. It was cooled to room temperature, and the content of the evaporator was recovered to obtain 26.7 kg of a product. The amount of the product was found to correspond to a yield of 90% by calculation, based on the staring material cyanuric acid used in step (A).

The product had an epoxide equivalent of 104 and formed a transparent liquid when molten at 140° C.

Step (E): The product obtained in step (D) was molten, and 100 g of the melt was gradually added to 400 g of methanol in a flask under agitation to form a solution of the product in methanol. The solution was heated to the reflux temperature of methanol, and then cooled to 5° C. over 12 hours to precipitate white crystals in the solution. The white crystals were separated by filtration and then dried to obtain 82 g of a final product. The final product had an epoxide equivalent of 100.

COMPARATIVE EXAMPLE 3

Steps (A) and (B) were conducted in the same manner as in Example 24, but in a reactor equipped with paddle blades. In step (B), precipitated sodium chloride attached to the side wall of the reactor, so that the reaction mixture was not maintained uniform. Steps (C) and (D) were conducted in the same manner as in Example 24, and 25.2 kg of a product was recovered from the evaporator. The product had an epoxide equivalent of 109. The product was treated in the same manner as in step (E) in Example 24 to obtain 80 g of white crystals as a dry final product. The final product had an epoxide equivalent of 101.

EXAMPLE 25

Step (A): Into a 20 l glass reactor equipped with an agitator having paddle blades, 300 g of water, 55 g of tetramethylammonium chloride, 13.88 kg of epichlorohydrin and 1.29 kg of cyanuric acid were put to form a reaction mixture. Then the reaction mixture was heated under agitation to raise its temperature.

When the temperature of the reaction mixture reached 89° C., the reaction mixture started to boil under atmospheric pressure. Heating was continued for 5 hours while the vapor generated was cooled with a condenser with all the liquefied epichlorohydrin continuously returned to the reactor and the liquefied water drained out of the reactor. When the temperature of the reaction mixture reached 120° C., heating was stopped, and the reaction mixture was cooled to obtain a reaction product at a temperature of 45° C. In the product, unreacted cyanuric acid was not detected.

Step (B): Then, dropwise addition of 2.56 kg of a 50 wt % sodium hydroxide aqueous solution to the whole reaction product maintained at 50° C. was started under a reduced pressure of 100 mmHg to form a reaction mixture, and at the same time, water and epichlorohydrin were evaporated from the reaction mixture.

The degree of vacuum was increased gradually, while the vapor was cooled with a condenser, all the liquefied epichlorohydrin was continuously returned to the reactor, and the liquefied water was drained out of the reactor. When the degree of vacuum reached 60 mmHg, the dropwise addition finished, and a slurry containing precipitated sodium chloride was obtained. The dropwise addition took 6 hours. After another 5 minutes of reflux, the vacuum in the reactor was released, and the agitation was stopped.

According to liquid chromatography analysis, the slurry thus obtained contained less than 1 wt % of a compound having a 2-hydroxy-3-chloropropyl group. Steps (A) and (B) were repeated 4 times, and all the slurry thus obtained was used for step (C).

Step (C): The above liquid product was gently agitated in a vessel together with 24 l of distilled water to dissolve the precipitated sodium chloride in the liquid product in the water added, and the liquid in the vessel was allowed to stand, and then the whole liquid product layer was recovered to obtain a partly refined liquid product.

The washing apparatus used in Example 14 was arranged for refining the liquid product further.

The partly refined liquid product was introduced into the washing apparatus until the upper reservoir was filled half, and the rotating shaft was rotated at a speed of 110 cycles per minute. An aqueous solution containing 3 wt % of sodium dihydrogenphosphate was supplied at a feed rate of 0.078 l/min, and when the aqueous solution which had been brought into contact with the liquid product started draining through the drain hole of the upper reservoir, draining of the liquid product from the bottom of the lower reservoir was started with supply of the unrefined liquid product through the liquid supply pipe on the upper part of the washing apparatus at a rate of 0.51 l/min. The liquid product recovered soon after the start of draining was returned to a storage tank for the partly refined liquid product, because it was not refined yet. It was observed that the supplied aqueous solution dispersed in the epichlorohydrin layer, forming droplets of about 0.3 to 7 mm in size. After the refined transparent liquid product started draining, the drained liquid was collected as a refined liquid.

Next, the refined liquid product was washed with distilled water. The refined liquid and water were supplied continuously at feed rates of 0.45 l/min and 0.19 l/min, respectively, while the rotating shaft was rotated at a speed of 110 cycles/min to obtain a second transparent liquid product. The epichlorohydrin layer obtained by the second washing was collected as the refined liquid product refined by step (C). The yield of triglycidyl isocyanurate was 90%.

Step (D); A 5 kg portion of the liquid product collected in step (C) was introduced to 10 l rotary evaporator. Evaporation of epichlorohydrin was started under reduced pressure at a temperature of 60° C., and continued while the degree of vacuum was increased gradually to 4 mmHg and the temperature of the liquid was elevated to 150° C. The liquid contained 500 ppm of epichlorohydrin and had an epoxide equivalent of 104. The product was transparent when molten at 140° C.

EXAMPLE 26

A liquid product containing precipitated sodium chloride was prepared in the same manner as in steps (A) and (B) in Example 25 except that 55 g of ethyltriphenylphosphonium bromide was used instead of 55 g of tetramethylammonium chloride. Steps (A) and (B) were repeated 4 times, and the whole slurry thus obtained was used for step (C).

Step (C) was conducted in the same manner as in Example 25. A partly refined liquid product was obtained firstly, and then the partly refined liquid product was refined to a high degree by means of the same washing apparatus as used in Example 14.

In the first washing in the washing apparatus, the rotation shaft was continuously rotated at a speed of 90 cycles/minute. A 3 wt % sodium dihydrogenphosphate aqueous solution was supplied through the liquid supply line of the lower reservoir at a rate of 0.052 l/min. After the aqueous solution which had been brought into contact with the liquid product started draining from the liquid outlet of the upper reservoir, draining of the liquid product from the bottom of the lower reservoir was started with supply of the partly refined liquid product through the liquid supply line at the top of the washing apparatus at a rate of 0.34 l/min. The liquid product recovered shortly after the start of draining was returned to the storage tank for the partly refined liquid product. It was observed that the supplied sodium dihydrogenphosphate aqueous solution was dispersed in the epichlorohydrin layer, forming droplets of 0.3 to 3 mm insides. After the transparent liquid product refined to a high degree started draining, all the drained liquid was collected as a liquid product refined to a high degree.

The liquid product refined to a high degree was then washed with distilled water. While the rotating shaft was rotated at a speed of 90 cycle/min, the liquid product and water were supplied continuously at rates of 0.30 l/min and 0.13 l/min, respectively, to obtain the second transparent liquid product. The epichlorohydrin layer obtained in the second washing was collected as a highly refined liquid product obtained by step (C).

Step (D): Epichlorohydrin was evaporated from the liquid product collected in step (C) in the same manner as in Example 25 to obtain a liquid product at 150° C. under a reduced pressure of 4 mmHg. The liquid contained 460 ppm of epichlorohydrin and had an epoxide equivalent of 105. The product was transparent when molten at 140° C.

EXAMPLE 27

Step (A): Into a 20 l glass reactor equipped with an agitator having paddle blades and baffles, 300 g of water, 55 g of tetramethylammonium chloride, 13.88 kg of epichlorohydrin and 1.29 kg of cyanuric acid were put to form a reaction mixture. Then the reaction mixture was heated under agitation to raise its temperature.

When the temperature of the reaction mixture reached 89° C., the reaction mixture started to boil under atmospheric pressure. Heating was continued for 5 hours while the vapor generated was cooled with a condenser with all the liquefied epichlorohydrin continuously returned to the reactor and the liquefied water drained out of the reactor. When the temperature of the reaction mixture reached 120° C., heating was stopped, and the reaction mixture was cooled to obtain a reaction product at a temperature of 45° C. In the product, unreacted cyanuric acid was not detected.

Step (B): Then, dropwise addition of 2.56 kg of a 50 wt % sodium hydroxide aqueous solution to the whole reaction product maintained at 50° C. was started under a reduced pressure of 100 mmHg to form a reaction mixture, and at the same time, water and epichlorohydrin were evaporated from the reaction mixture.

The degree of vacuum was increased gradually, while the vapor was cooled with a condenser, all the liquefied epichlorohydrin was continuously returned to the reactor, and the liquefied water was drained out of the reactor. When the degree of vacuum reached 60 mmHg, the dropwise addition finished, and a liquid product containing precipitated sodium chloride was obtained. The dropwise addition took 6 hours. After another 5 minutes of reflux, the vacuum in the reactor was released, and the agitation was stopped.

According to liquid chromatography analysis, the liquid product thus obtained contained less than 1 wt % of a compound having a 2-hydroxy-3-chloropropyl group.

Step (C): The whole liquid product obtained in step (B) was washed three times. Firstly, it was agitated with 6 kg of distilled water and then allowed to stand for 24 hours. Secondly, it was agitated with 6 kg of a 5 wt % sodium dihydrogenphosphate aqueous solution and then allowed to stand 24 hours. Finally, it was agitated with 8 kg of distilled water and then allowed to stand for 24 hours. The final epichlorohydrin layer was recovered as a refined liquid product.

Step (D): The liquid product obtained in step (C) was treated in a flash evaporator to obtain a concentrate having an epichlorohydrin concentration of 50 wt %. Epichlorohydrin was evaporated from a film of the concentrate by means of the evaporator used in Example 15 to obtain a product of triglycidyl isocyanurate having a reduced epichlorohydrin concentration. The yield of triglycidyl isocyanurate was 90%, based on the starting material isocyanuric acid.

Heating steam was introduced into the jacket of the evaporator, the rotating shaft was rotated at a speed of 200 rpm, and the evacuator was started. The concentrate of the liquid product having an epichlorohydrin concentration of 50 wt % obtained in the flash evaporator was supplied to the evaporator. The evaporator was run at feed rates and degree of vacuum shown in Table 1 with the film thicknesses ($\mu$) and average retention times shown in the Table, and products ($P_1$) and ($P_2$) having the temperatures at the outlet in the bottom of the evaporator, the epoxide equivalents and the epichlorohydrin concentrations (ECHppm) shown in the Table were recovered from the outlet in the bottom of the evaporator. The recovered products were both transparent liquids containing no insoluble matters.

Then, the recovered liquid product ($P_1$) was treated again in the evaporator to obtain a product ($Q_1$) having a still lower epihalohydrin concentration. This time, the liquid was supplied at a feed rate of 14.0 kg/hr, and the rotating shaft was rotated at a speed of 200 rpm. The evaporator was run at the degree of vacuum shown in Table 1 with the film thickness ($\mu$) and the average retention time shown in the Table, the product ($Q_1$) having the temperature at the outlet in the bottom of the evaporator, the epoxide equivalent and the epichlorohydrin concentration (ECHppm) shown in the Table was recovered from the outlet in the bottom of the evaporator. The recovered product was a transparent liquid containing no insoluble matters.

TABLE 1

| Evaporation conditions and properties of product | Recovered product | | |
|---|---|---|---|
| | $P_1$ | $P_2$ | $Q_1$ |
| Supplied liquid | Concentrate | Concentrate | p1 |
| Feed rate (kg/hr) | 21.7 | 7.3 | 14.0 |
| Degree of vacuum (mmHg) | 10 | 10 | 0.2 |
| Film thickness ($\mu$) | 450 | 150 | 170 |
| Retention time (sec) | 15 | 15 | 18 |
| Temperature of product at outlet (°C.) | 120 | 137 | 150 |
| Epoxide equivalent of product | 103 | 103 | 103 |
| ECH concentration of product (ppm) | 3800 | 2000 | 80 |

Step (E): 100 g of the melt of the product ($Q_1$) obtained in step (D) was gradually added to 400 g of methanol in a flask under agitation to form a solution of the product in methanol. The solution was heated to the reflux temperature of methanol, and then cooled to 5° C. over 12 hours to precipitate white crystals in the solution. The white crystals were separated by filtration and then dried to obtain 82 g of a final product ($Z_1$) having an epoxide equivalent of 99.

COMPARATIVE EXAMPLE 4

A refined liquid product was obtained in the same manner as in steps (A) to (C) in Example 27 and then it was treated in a flash evaporator to obtain a concentrate having an epichlorohydrin concentration of 50 wt %.

Next, 5 kg of the concentrate was introduced in a 10 l rotary evaporator, removal of epichlorohydrin was started at a reduced pressure of 100 mmHg at 60° C. The removal of epichlorohydrin was continued while the degree of vacuum was increased gradually and the temperature was elevated. The temperature of the liquid in the evaporator reached 150° C. under a reduced pressure of 4 mmHg 4 hours after the start of the evaporation. The resulting liquid contained 500 ppm of epichlorohydrin and had an epoxide equivalent of 104. Epichlorohydrin was evaporated for another 4 hours at 160° C. at a lower pressure of 2 mmHg, and the resulting liquid contained 200 ppm of epichlorohydrin and had an increased epoxide equivalent of 107.

EXAMPLE 28

Example 24 was reproduced on a scale enlarged by 25 times by using a reactor having an internal volume of 5 m³.

Step (A) could be carried out smoothly in the same manner as in Example 24. In step (B), the reaction mixture was maintained uniform without adhesion of precipitated sodium chloride to the side wall of the reactor unlike Comparative Example 3.

Steps (C) and (D) were conducted in the same manner as in Example 24 to obtain a product in a yield of 90%. The product had an epoxide equivalent of 104. Step (E) was conducted in the same manner as in Example 24 to obtain a product in a 82% yield. The product had an epoxide equivalent of 100.

EXAMPLE 29

A slurry containing precipitated sodium chloride was prepared in the same manner as in steps (A) and (B) in Example 13.

The whole slurry was gently agitated together with 90 kg of water to dissolve the precipitated sodium chloride in the slurry in the water added, and the liquid in the vessel was allowed to stand. The whole organic layer was recovered to obtain a transparent liquid. Then, the liquid was refined by means of the washing apparatus used in step (C) in Example 14 with an aqueous solution containing 3 wt % of sodium dihydrogenphosphate and no sodium toluenesulfonate at first, and then with distilled water, to obtain a refined liquid.

The refined liquid was treated in a flash evaporator at a higher rate in the same manner as in step (D) in Example 15, and epichlorohydrin was removed by means of a film evaporator to obtain 26.7 kg of a product having an epoxide equivalent of 104 and an epichlorohydrin concentration of 60 ppm.

The melt of the product at 140° C. was transparent.

According to the present invention, it is possible to produce a 2,3-epoxypropyl derivative or a 2-methyl-2,3-epoxypropyl derivative of a compound having from 2 to 4 carboxyl groups or a compound having from 1 to 3 amido groups as a purified product. The product has a high oxirane oxygen content, is fairly transparent when molten, and has such a high heat stability that it does not change in epoxide equivalent when heated at 150° C. for 24 hours. A product having such a high purity and a high heat stability can be preferably used as a transparent sealer for semiconductor devices such as light emitting devices, light intercepting devices or photoelectric transfer devices.

According to the method of the present invention, the above-mentioned purified product can be produced with high production efficiency, for example, at a high product yield, a high recovery of a epihalohydrin or a 2-methylepihalohydrin in a short time, and the waste water produced in the method is easy to handle, because it contains small amounts of an epihalohydrin or a 2-methleihalohydrin and the epoxy compound.

We claim:

1. A method for producing from a compound having in its molecule 2 to 4 carboxyl groups or 1 to 3 amido groups the 2,3-epoxypropyl derivative or the 2-methyl-2,3-epoxypropyl derivative in which all of the hydrogen atoms in the carboxyl groups or the amido groups are replaced by 2,3-epoxypropyl groups or 2-methyl-2,3-epoxypropyl groups as a purified product which has an epoxide equivalent of 1.0 to 1.1 times the theoretical epoxide equivalent of the derivative and an ionic halogen content of 10 ppm or less, forms a transparent liquid when molten, and shows increasing in epoxide equivalent by at most 3% when stored at 150° C. for 24 hours, comprising steps (A) to (D):

(A) reacting an epihalohydrin or a 2-methyl-epihalohydrin with a compound having in its molecule in its molecule 2 to 4 carboxyl groups or 1 to 3 amido groups in a reaction mixture containing the compound and the epihalohydrin or the 2-methyl-epihalohydrin in a ratio of 1 mol of active hydrogen atoms of the carboxyl groups or the amido groups of the compound to 1.2 to 60 mol of the epihalohydrin or the 2-methyl-epihalohydrin, and a catalytic amount of a tertiary amine, a quaternary ammonium base or salt, a tri-substituted phosphine or a quaternary phosphonium salt, thereby forming a reaction product containing a 2-hydroxy-3-halopropyl derivative or a 2-hydroxy-2-methyl-3-halopropyl derivative of the compound, (B) adding gradually to the reaction product an alkali metal hydroxide in a ratio of 1 to 2 mol of the hydroxide to 1 mol of active hydrogen atoms of the carboxyl groups or the amido groups of the compound in the reaction product before the reaction in step (A) to cause and complete dehydrohalogenation to the derivative while agitating the resulting slurry containing a pre-cipitated alkali metal halide, thereby forming a final slurry containing the 2,3-epoxypropyl derivative or the 2-methyl-2,3-epoxypropyl derivative of the compound and an alkali metal halide produced by the dehydrohalogenation, (C) washing the final slurry obtained in step (B) or a liquid product obtained by removing the alkali metal halide from the final slurry in step (B) with an aqueous solution of, as refining agent, a sulfonic acid, a salt of a sulfonic acid, a salt of a carboxylic acid having at least 7 carbon atoms in the molecule, a salt of a sulfate of an alcohol having at least 4 carbon atoms in the molecule or a mixture thereof respectively having a solubility of at least 1 wt % in water at 30° C., said solution containing the refining agent in an amount effective for refining the slurry or the liquid product, thereby forming a refined liquid containing the deriva-tive formed in step (B), and (D) removing by evaporation the epihalohydrin or the 2-methyl-epihalohidrin in the refined liquid obtained in step (C), thereby forming the 2,3-epoxypropyl deriva-tive or the 2-methyl-2,3-epoxypropyl derivative of the compound as the purified product.

2. The method for producing the derivative as claimed in claim 1, wherein step (B) is carried out in a vessel by a process comprising adding the alkali metal hydroxide as an aqueous solution having a concentration of 20 to 70 wt % of the hydroxide, and maintaining the slurry under agitation which causes the slurry to produce a stream circulating and ascending from the bottom along the inner side wall of the vessel to the surface of the slurry, turning there the ascend-ing stream to a stream swirling downward and shearing across the swirling stream, thereby maintaining the slurry uniform, while removing by evaporation from the slurry the water added and generated by the reaction in a vacuum at a temperature of 10 to 80° C.

3. The method for producing the derivative as claimed in claim 1, wherein the washing in step (C) is carried out for the liquid product by a process comprising introducing into a column of the liquid product droplets of the aqueous solution having a mean diameter of 0.1 to 10 mm, allowing the droplets to ascend and thereafter to unify to form a layer of the aqueous solution in the column, repeating stepwise the cycle consisting of the introducing, the ascending and the unification of the droplets in the column, and continuing supplying to the liquid product the aqueous solution by the introduction thereof until 0.01 to 5 parts by weight of the refining agent relative to 100 parts by weight of the deriva-tive in the liquid product is supplied to the liquid product, thereby causing refining of the liquid product.

4. The method for producing the derivative as claimed in claim 1, wherein the evaporation in step (D) is carried out by a process comprising forming by coating on a surface of a substrate a film of the refined liquid or the concentrate thereof having a thickness of 30 to 500 $\mu$m and having at one end of the film the highest concentration and gradually lowered concentration toward the lowest concentration at the opposite end of the film respectively of the volatile components in the refined liquid or the concentrate thereof, and evaporating from the film the volatile components under a pressure of 5 mmHg or lower of the components at 100° to 165° C., while supplying continuously to the end of the film having the highest concentration of the volatile com-ponents the refined liquid or the concentrate thereof, con-veying gradually toward the opposite end the liquid under the evaporation and the film thickness, and recovering continuously from the opposite end of the film a final liquid having a lowered concentration of the volatile components.

5. The method for producing the derivative as claimed in claim 3, wherein step (B) is carried out in a vessel by a process comprising adding the alkali metal hydroxide as an aqueous solution having a concentration of 20 to 70 wt % of the hydroxide, and maintaining the slurry under agitation which causes the slurry to produce a stream circulating and ascending from the bottom along the inner side wall of the vessel to the surface of the slurry, turning there the ascend-ing stream to a stream swirling downward and shearing across the swirling stream, thereby maintaining the slurry uniform, while removing by evaporation from the slurry the water added and generated by the reaction in a vacuum at a temperature of 10° to 80° C.

6. The method for producing the derivative as claimed in claim 4, wherein the washing in step (C) is carried out for the liquid product by a process comprising introducing into a column of the liquid product droplets of the aqueous solution having a mean diameter of 0.1 to 10 mm, allowing the droplets to ascend and thereafter to unify to form a layer of the aqueous solution in the column, repeating stepwise the cycle consisting of the introducing, the ascending and the unification of the droplets in the column, and continuing supplying to the liquid product the aqueous solution by the introduction thereof until 0.01 to 5 parts by weight of the refining agent to 100 parts by weight of the derivative in the liquid product is supplied to the liquid product, thereby causing refining of the liquid product.

7. The method for producing the derivative as claimed in claim 2, wherein the evaporation in step (D) is carried out by a process comprising forming by coating on a surface of a substrate a film of the refined liquid or the concentrate thereof having a thickness of 30 to 500 $\mu$m and having at one end of the film the highest concentration and gradually lowered concentration toward the lowest concentration at the opposite end of the film respectively of the volatile components in the refined liquid or the concentrate thereof, and evaporating from the film the volatile components under a pressure of 5 mmHg or lower of the components at 100° to 165° C., while supplying continuously to the end of the film having the highest concentration of the volatile com-ponents the refined liquid or the concentrate thereof, con-veying gradually toward the opposite end the liquid under the evaporation and the film thickness, and recovering continuously from the opposite end of the film a final liquid having a lowered concentration of the volatile components.

8. The method for producing the derivative as claimed in claim 2, wherein the washing in step (C) is carried out for the liquid product by a process comprising introducing into a column of the liquid product droplets of the aqueous solution having a mean diameter of 0.1 to 10 mm, allowing the droplets to ascend and thereafter to unify to form a layer of the aqueous solution in the column, repeating stepwise the cycle consisting of the introducing, the ascending and the unification of the droplets in the column, and continuing supplying to the liquid product the aqueous solution by the introduction thereof until 0.01 to 5 parts by weight of the refining agent relative to 100 parts by weight of the derivative in the liquid product is supplied to the liquid product, thereby causing refining of the liquid product, and the evaporation in step (D) is carried out by a process comprising forming by coating on a surface of a substrate a film of the refined liquid or the concentrate thereof having a thickness of 30 to 500 µm and having at one end of the film the highest concentration and gradually lowered concentration toward the lowest concentration at the opposite end of the film respectively of the volatile components in the refined liquid or the concentrate thereof, and evaporating from the film the volatile components under a pressure of 5 mmHg or lower of the components at 100° to 165° C., while supplying continuously to the end of the film having the highest concentration of the volatile components the refined liquid or the concentrate thereof, conveying gradually toward the opposite end the liquid under the evaporation and the film thickness, and recovering continuously from the opposite end of the film a final liquid having a lowered concentration of the volatile components.

9. The method for producing the derivative as claimed in any of claims 1 to 8, wherein the reaction in step (A) is continued until 90% or more of the active hydrogen atoms disappear in the reaction mixture.

10. The method for producing the derivative as claimed in any of claims 1 to 8, wherein the refining agent in step (C) is benzenesulfonic acid or toluenesulfonic acid, or a salt of benzenesulfonic acid, toluenesulfonic acid, vinylsulfonic acid, a polymer of vinylsulfonic acid, a polycondensate of naphthalenesulfonic acid and formaldehyde, tetrahydrophthalic acid, lauryl sulfate, phthalic acid, salicylic acid or cinnamic acid.

11. The method for producing the derivative as claimed in any of claims 1 to 8, wherein the compound in step (A) is terephthalic acid, and the derivative in step (D) is bis(2,3-epoxypropyl) terephthalate or bis(2-methyl-2,3-epoxypropyl) terephthalate.

12. The method for producing the derivative as claimed in any of claims 1 to 8, wherein the compound in step (A) is isocyanuric acid, and the derivative in step (D) is tris(2,3-epoxypropyl) isocyanurate or tris(2-methyl-2,3-epoxypropyl) isocyanurate.

13. A method for producing bis(2,3-epoxypropyl) terephthalate or bis(2-methyl-2,3-epoxypropyl) terephthalate as a product more purified than the product obtained in step (D) in claim 11, comprising adding to step (D) in claim 11 the following step (E):

(E) forming a solution of the product obtained in step (D) in claim 11 by dissolving the product in a solvent, precipitating the derivative in the crystalline form out of the solution, and removing from the solution and drying the precipitate.

14. A method for producing tris(2,3-epoxypropyl) isocyanurate or tris(2-methyl-2,3-epoxypropyl) isocyanurate as a product more purified than the product obtained in step (D) in claim 12, comprising adding to step (D) in claim 12 the following step (E):

(E) forming a solution of the product obtained in step (D) in claim 12 by dissolving the product in a solvent, precipitating the derivative in the crystalline form out of the solution, and removing from the solution and drying the precipitate.

15. A method for producing tris(2,3-epoxypropyl) isocyanurate or tris(2-methyl-2,3-epoxypropyl) isocyanurate as a purified product which has an epoxide equivalent of 1.0 to 1.1 times the theoretical epoxide equivalent of the isocyanurate and forms a transparent liquid when molten, comprising steps (A) to (D):

(A) reacting an epihalohydrin or a 2-methyl-epihalohydrin with isocyanuric acid in a reaction mixture containing isocyanuric acid and the epihalohydrin or the 2-methyl-epihalohydrin in a ratio of 1 mol of active hydrogen atoms of the isocyanuric acid to 1.2 to 60 mol of the epihalohydrin or the 2-methyl-epihalohydrin, and a catalytic amount of a tertiary amine, a quaternary ammonium base or salt, a tri-substituted phosphine or a quaternary phosphonium salt, thereby forming a reaction product containing a tris(2-hydroxy-3-halopropyl) isocyanurate or a tris(2-hydroxy-2-methyl-3-halopropyl) isocyanurate, (B) adding gradually to the reaction product in a vessel an alkali metal hydroxide as an aqueous solution having a concentration of 20 to 70 wt % of the hydroxide in a ratio of 1 to 2 mol of the hydroxide to 1 mol of active hydrogen atoms of the isocyanuric acid in the reaction product before the reaction in step (A) to cause and complete dehydrohalogenation to the isocyanurate in the reaction product and to form a slurry containing a precipitated alkali metal halide, while maintaining the slurry under agitation which causes the slurry to produce a stream circulating and ascending from the bottom along the inner side wall of the vessel to the surface of the slurry, turning there the ascending stream to a stream swirling downward and shearing across the swirling stream, thereby maintaining the slurry uniform, and removing by evaporation from the slurry the water added and caused by the reaction in a vacuum at a temperature of 10° to 80° C., thereby forming a final slurry containing tris(2,3-epoxypropyl) isocyanurate or tris(2-methyl-2,3-epoxypropyl) isocyanurate and an alkali metal halide generated by the reaction, (C) washing with water the final slurry in step (B) or a liquid product obtained by removing the alkali metal halide from the final slurry in step (B), thereby forming a refined liquid containing the isocyanurate, and (D) removing by evaporation the epihalohydrin or the 2-methyl-epihalohidrin from the refined liquid obtained in step (C), thereby forming tris(2,3-epoxypropyl) isocyanurate or tris(2-methyl-2,3-epoxypropyl) isocyanurate as the purified product.

16. A method for producing tris(2,3-epoxypropyl) isocyanurate or tris(2-methyl-2,3-epoxypropyl) isocyanurate as a purified product which has an epoxide equivalent of 1.0 to 1.1 times the theoretical epoxide equivalent of the isocyanurate and forms a transparent liquid when molten, comprising steps (A) to (D):

(A) reacting an epihalohydrin or a 2-methyl-epihalohydrin with isocyanuric acid in a reaction mixture containing the isocyanuric acid and the epihalohydrin or the 2-methyl-epihalohydrin in a ratio of 1 mol of active hydrogen atoms of the isocyanuric acid to 1.2 to 60 mol of the epihalohydrin or the 2-methyl-epihalohydrin, and a catalytic amount of a tertiary amine, a quaternary ammonium base or salt, a tri-substituted phosphine or a quaternary phosphonium salt, thereby forming a reaction product containing a tris(2-hydroxy-3-halopropyl) isocyanurate or a tris(2-hydroxy-2-methyl-3-halopropyl) isocyanurate, (B) adding gradually to the reaction product an alkali metal hydroxide in a ratio of 1 to 2 mol of the hydroxide to 1 mol of active hydrogen atoms of the isocyanuric acid in the reaction product before the reaction in step (A) to cause and complete dehydrohalogenation to the isocyanurate while agitating the resulting slurry containing a precipitated alkali metal halide, thereby forming a final slurry containing tris(2,3-epoxypropyl) isocyanurate or tris(2-methyl-2,3-epoxypropyl) isocyanurate and an alkali metal halide produced by the reaction, (C) washing with water a liquid product obtained by removing the alkali metal halide from the final slurry in step (B) by a process comprising introducing into a column of the liquid product water droplets having a mean a diameter of 0.1 to 10 mm, allowing the droplets to ascend and thereafter to unify to form an aqueous layer in the column, repeating stepwise the cycle consisting of the introducing, the ascending and the unification of the droplets in the column, and continuing supplying to the liquid product water by the introduction thereof until 50 to 5000 parts by weight of the water relative to 100 parts by weight of the isocyanurate in the liquid product is supplied to the liquid product, thereby forming a refined liquid containing the isocyanurate, and (D) removing by evaporation the epihalohydrin or the 2-methyl-epihalohidrin from the refined liquid obtained in step (C), thereby forming tris(2,3-epoxypropyl) isocyanurate or tris(2-methyl-2,3-epoxypropyl) isocyanurate as the purified product.

17. A method for producing tris(2,3-epoxypropyl) isocyanurate or tris(2-methyl-2,3-epoxypropyl) isocyanurate as a purified product which has an epoxide equivalent of 1.0 to 1.1 times the theoretical epoxide equivalent of the isocyanurate and forms a transparent liquid when molten, comprising steps (A) to (D):

(A) reacting an epihalohydrin or a 2-methyl-epihalohydrin with isocyanuric acid in a reaction mixture containing the isocyanuric acid and the epihalohydrin or the 2-methyl-epihalohydrin in a ratio of 1 mol of active hydrogen atoms of the isocyanuric acid to 1.2 to 60 mol of the epihalohydrin or the 2-methyl-epihalohydrin, and a catalytic amount of a tertiary amine, a quaternary ammonium base or salt, a tri-substituted phosphine or a quaternary phosphonium salt, thereby forming a reaction product containing the resulting tris(2-hydroxy-3-halopropyl) isocyanurate or tris(2-hydroxy-2-methyl-3-halopropyl) isocyanurate, (B) adding gradually to the reaction product an alkali metal hydroxide in a ratio of 1 to 2 mol of the hydroxide to 1 mol of active hydrogen atoms of the isocyanuric acid in the reaction product before the reaction in step (A) to cause and complete dehydrohalogenation to the isocyanurate while agitating the resulting slurry containing a precipitated alkali metal halide, thereby forming a final slurry containing tris(2,3-epoxypropyl) isocyanurate or tris(2-methyl-2,3-epoxypropyl) isocyanurate and an alkali metal halide generated by the reaction, (C) washing with water the final slurry in step (B) or a liquid product obtained by removing the alkali metal halide from the final slurry in step (B), thereby forming a refined liquid containing the isocyanurate, and (D) removing the epihalohydrin or the 2-methyl-epihalohydrin from the refined liquid obtained in step (C), by a process comprising forming by coating on a surface of a substrate a film of the refined liquid or the concentrate thereof having a thickness of 30 to 500 µm and having at one end of the film the highest concentration and gradually lowered concentration toward the lowest concentration at the opposite end of the film respectively of the volatile components in the refined liquid or the concentrate thereof, and evaporating from the film the volatile components under a pressure of 5 mmHg or lower of the components at 100° to 165° C., while supplying continuously to the end of the film having the highest concentration of the volatile components the refined liquid or the concentrate thereof, conveying gradually toward the opposite end the liquid under the evaporation and the film thickness, and recovering continuously from the opposite end of the film a final liquid having a lowered concentration of the volatile components, thereby forming tris(2,3-epoxypropyl) isocyanurate or tris(2-methyl-2,3-epoxypropyl) isocyanurate as the purified product.

18. The method for producing tris(2,3-epoxypropyl) isocyanurate or tris(2-methyl-2,3-epoxypropyl) isocyanurate as claimed in claim 15, wherein the washing in step (C) is carried out for the liquid product by a process comprising introducing into a column of the liquid product water droplets having a mean diameter of 0.1 to 10 mm, allowing the droplets to ascend and thereafter to unify to form an aqueous layer in the column, repeating stepwise the cycle consisting of the introducing, the ascending and the unification of droplets in the column, and continuing supplying to the liquid product water by the introduction thereof until 50 to 5000 parts by weight of water to 100 parts by weight of the isocyanurate in the liquid product is supplied to the liquid product, thereby forming a refined liquid containing the isocyanurate.

19. The method for producing tris(2,3-epoxypropyl) isocyanurate or tris(2-methyl-2,3-epoxypropyl) isocyanurate as claimed in claim 15, wherein the evaporation in step (D) is carried out by a process comprising forming by coating on a surface of a substrate a film of the refined liquid or the concentrate thereof having a thickness of 30 to 500 µm and having at one end of the film the highest concentration and gradually lowered concentration toward the lowest concentration at the opposite end of the film respectively of the volatile components in the refined liquid or the concentrate thereof, and evaporating from the film the volatile components under a pressure of 5 mmHg or lower of the components at 100° to 165° C., while supplying continuously to the end of the film having the highest concentration of the volatile components the refined liquid or the concentrate thereof, conveying gradually toward the opposite end the liquid under the evaporation and the film thickness, and recovering continuously from the opposite end of the film a final liquid having a lowered concentration of the volatile components, thereby forming tris(2,3-epoxypropyl) isocyanurate or tris(2-methyl-2,3-epoxypropyl) isocyanurate as the purified product.

20. A method for producing tris(2,3-epoxypropyl) isocyanurate or tris(2-methyl-2,3-epoxypropyl) isocyanurate, comprising adding to step (D) in any of claims 15 to 19 the following step (E):

(E) forming a solution of the product obtained in step (D) by dissolving the product in a solvent, precipitating the derivative in the crystalline form out of the solution, and removing from the solution and drying the precipitate, thereby forming a product more purified than the product in the step (D).

21. A method for producing bis(2,3-epoxypropyl) terephthalate or bis(2-methyl-2,3-epoxypropyl) terephthalate as a purified product which has an epoxide equivalent of 1.0 to 1.1 times the theoretical epoxide equivalent of the terephthalate and forms a transparent liquid when molten, comprising steps (A) to (D):

(A) reacting an epihalohydrin or a 2-methyl-epihalohydrin with terephthalic acid in a reaction mixture containing the terephthalic acid and the epihalohydrin or the 2-methyl-epihalohydrin in a ratio of 1 mol of active hydrogen atoms of the terephthalic acid to 1.2 to 60 mol of the epihalohydrin or the 2-methyl-epihalohydrin, and a catalytic amount of a tertiary amine, a quaternary ammonium base or salt, a tri-substituted phosphine, a quaternary phosphonium salt or an alkali metal halide, thereby forming a reaction product containing a bis(2-hydroxy-3-halopropyl) terephthalate or a bis(2-hydroxy-2-methyl-3-halopropyl) terephthalate, (B) adding gradually to the reaction product in a vessel an alkali metal hydroxide as an aqueous solution having a concentration of 20 to 70 wt % of the hydroxide in a ratio of 1 to 2 mol of the hydroxide to 1 mol of active hydrogen atoms of the terephthalic acid in the reaction product before the reaction in step (A) to cause and complete dehydrohalogenation to the terephthalate in the reaction product and to form a slurry containing a precipitated alkali metal halide, while maintaining the slurry under agitation which causes the slurry to produce a stream circulating and ascending from the bottom along the inner side wall of the vessel to the surface of the slurry, turning there the ascending stream to a stream swirling downward and shearing across the swirling stream, thereby maintaining the slurry uniform, and removing by evaporation from the slurry the water added and caused by the reaction under a vacuum at a temperature of 10° to 80° C., thereby forming a final slurry containing bis(2,3-epoxypropyl) terephthalate or bis(2-methyl-2,3-epoxypropyl) terephthalate and an alkali metal halide generated by the reaction, (C) washing with water the final slurry in step (B) or a liquid product obtained by removing the alkali metal halide from the final slurry in step (B), thereby forming a refined liquid containing the terephthalate, and (D) removing by evaporation the epihalohydrin or the 2-methyl-epihalohidrin from the refined liquid obtained in step (C), thereby forming bis(2,3-epoxypropyl) terephthalate or bis(2-methyl-2,3-epoxypropyl) terephthalate as the purified product.

22. A method for producing bis(2,3-epoxypropyl) terephthalate or bis(2-methyl-2,3-epoxypropyl) terephthalate as a purified product which has an epoxide equivalent of 1.0 to 1.1 times the theoretical epoxide equivalent of the terephthalate and forms a transparent liquid when molten, comprising steps (A) to (D):

(A) reacting an epihalohydrin or a 2-methyl-epihalohydrin with terephthalic acid in a reaction mixture containing the terephthalic acid and the epihalohydrin or the 2-methyl-epihalohydrin in a ratio of 1 mol of active hydrogen atom of the terephthalic acid to 1.2 to 60 mol of the epihalohydrin or the 2-methyl-epihalohydrin, and a catalytic amount of a tertiary amine, a quaternary ammonium base or salt, a tri-substituted phosphine, a quaternary phosphonium salt or an alkali metal halide, thereby forming a reaction product containing a bis(2-hydroxy-3-halopropyl) terephthalate or a bis(2-hydroxy-2-methyl-3-halopropyl) terephthalate, (B) adding gradually to the reaction product an alkali metal hydroxide in a ratio of 1 to 2 mol of the hydroxide to 1 mol of active hydrogen atoms of the terephthalic acid in the reaction product before the reaction in step (A) to cause and complete dehydrohalogenation to the terephthalate while agitating the resulting slurry containing a precipitated alkali metal halide, thereby forming a final slurry containing bis(2,3-epoxypropyl) terephthalate or bis(2-methyl-2,3-epoxypropyl) terephthalate and an alkali metal halide generated by the reaction, (C) washing with water a liquid product obtained by removing the alkali metal halide from the final slurry in step (B) by a process comprising introducing into a column of the liquid product water droplets having a mean diameter of 0.1 to 10 mm, allowing the droplets to ascend and thereafter to unify to form an aqueous layer in the column, repeating stepwise the cycle consisting of the introducing, the ascending and the unification of water droplets in the column, and continuing supplying to the liquid product water by the introduction thereof until 50 to 5000 parts by weight of water to 100 parts by weight of the terephthalate in the liquid product is supplied to the liquid product, thereby forming a refined liquid containing the terephthalate, and (D) removing by evaporation the epihalohydrin or the 2-methyl-epihalohidrin from the refined liquid obtained in step (C), thereby forming bis(2,3-epoxypropyl) terephthalate or bis(2-methyl-2,3-epoxypropyl) terephthalate as the purified product.

23. A method for producing bis(2,3-epoxypropyl) terephthalate or bis(2-methyl-2,3-epoxypropyl) terephthalate as a purified product which has an epoxide equivalent of 1.0 to 1.1 times the theoretical epoxide equivalent of the terephthalate and forms a transparent liquid when molten, comprising steps (A) to (D):

(A) reacting an epihalohydrin or a 2-methyl-epihalohydrin with terephthalic acid in a reaction mixture containing terephthalic acid and the epihalohydrin or the 2-methyl-epihalohydrin in a ratio of 1 mol of active hydrogen atoms of the terephthalic acid to 1.2 to 60 mol of the epihalohydrin or the 2-methyl-epihalohydrin, and a catalytic amount of a tertiary amine, a quaternary ammonium base or salt, a tri-substituted phosphine, a quaternary phosphonium salt or an alkali metal halide, thereby forming a reaction product containing a bis(2-hydroxy-3-halopropyl) terephthalate or a bis(2-hydroxy-2-methyl-3-halopropyl) terephthalate, (B) adding gradually to the reaction product an alkali metal hydroxide in a ratio of 1 to 2 mol of the hydroxide to 1 mol of active hydrogen atoms of the terephthalic acid in the reaction product before the reaction in step (A) to cause and complete dehydrohalogenation to the terephthalate while agitating the resulting slurry containing a precipitated alkali metal halide, thereby forming a final slurry containing bis(2,3-epoxypropyl) terephthalate or bis(2-methyl-2,3-epoxypropyl) terephthalate and an alkali metal halide generated by the reaction, (C) washing with water the final slurry in step (B) or a liquid product obtained by removing the alkali metal halide from the final slurry in step (B), thereby forming a refined liquid containing the terephthalate, and (D) removing the epihalohydrin or the 2-methyl-epihalohidrin from the refined liquid obtained in step (C), by a process comprising forming by coating on a surface of a substrate a film of the refined liquid or the concentrate thereof having a thickness of 30 to 500 μm and having at one end of the film the highest concentration and gradually lowered concentration toward the lowest concentration at the opposite end of the film respectively of the volatile components in the refined liquid or the concentrate thereof, and evaporating from the film the volatile components under a pressure of 5 mmHg or lower of the components at 100° to 165° C., while supplying continuously to the end of the film having the highest concentration of the volatile components the refined liquid or the concentrate thereof, conveying gradually toward the opposite end the liquid under the evaporation and the film thickness, and recovering continuously from the opposite end of the film a final liquid having a lowered concentration of the volatile components, thereby forming bis(2,3-epoxypropyl) terephthalate or bis(2-methyl-2,3-epoxypropyl) terephthalate as the purified product.

24. The method for producing bis(2,3-epoxypropyl) terephthalate or bis(2-methyl-2,3-epoxypropyl) terephthalate as claimed in claim 21, wherein the washing in step (C) is carried out for the liquid product by a process comprising introducing into a column of the liquid product water droplets having a mean diameter of 0.1 to 10 mm, allowing the droplets to ascend and thereafter to unify to form an aqueous layer in the column, repeating stepwise the cycle consisting of the introducing, the ascending and the unification of water droplets in the column, and continuing supplying to the liquid product water by the introduction thereof until 50 to 5000 parts by weight of water to 100 parts by weight of the terephthalate in the liquid product is supplied to the liquid product, thereby forming a refined liquid containing the terephthalate.

25. The method for producing bis(2,3-epoxypropyl) terephthalate or bis(2-methyl-2,3-epoxypropyl) terephthalate as claimed in claim 21, wherein the evaporation in step (D) is carried out by a process comprising forming by coating on a surface of a substrate a film of the refined liquid or the concentrate thereof having a thickness of 30 to 500 μm and having at one end of the film the highest concentration and gradually lowered concentration toward the lowest concentration at the opposite end of the film respectively of the volatile components in the refined liquid or the concentrate thereof, and evaporating from the film the volatile components under a pressure of 5 mmxg or lower of the components at 100° to 165° C., while supplying continuously to the end of the film having the highest concentration of the volatile components the refined liquid or the concentrate thereof, conveying gradually toward the opposite end the liquid under the evaporation and the film thickness, and recovering continuously from the opposite end of the film a final liquid having a lowered concentration of the volatile components, thereby forming bis(2,3-epoxypropyl) terephthalate or bis(2-methyl-2,3-epoxypropyl) terephthalate as the purified product.

26. A method for producing bis(2,3-epoxypropyl) terephthalate or bis(2-methyl-2,3-epoxypropyl) terephthalate, comprising adding to step (D) in any of claims 21 to 25 the following step (E):

(E) forming a solution of the product obtained in the step (D) by dissolving the product in a solvent, precipitating the derivative in the crystalline form out of the solution, and removing from the solution and drying the precipitate, thereby forming a product more purified than the product in the step (D).

* * * * *